United States Patent

Kobayashi et al.

[11] Patent Number: 5,948,662
[45] Date of Patent: Sep. 7, 1999

[54] BACILLUS-DERIVED TRANSGLUTAMINASE

[75] Inventors: Katsunori Kobayashi; Shigeru Yamanaka; Kiyoshi Miwa; Shunichi Suzuki; Yuzuru Eto; Yuko Tanita; Kenzo Yokozeki; Kenichi Hashiguchi, all of Kawasaki, Japan

[73] Assignee: Ajinomoto Co., Inc., Tokyo, Japan

[21] Appl. No.: 08/989,667

[22] Filed: Dec. 12, 1997

Related U.S. Application Data

[62] Division of application No. 08/596,864, Feb. 9, 1996, Pat. No. 5,731,183.

[30] Foreign Application Priority Data

Feb. 9, 1995  [JP]  Japan ..................................... 7-021963
Sep. 4, 1995  [JP]  Japan ..................................... 7-226316
Jan. 29, 1996 [JP]  Japan ..................................... 8-013072

[51] Int. Cl.$^6$ .............................. C12N 9/10; C12N 15/54
[52] U.S. Cl. ................. 435/193; 435/320.1; 435/325; 435/419; 435/252.3; 536/23.2
[58] Field of Search ...................... 536/23.2; 435/320.1, 435/325, 193, 68.1, 252.3, 419

[56] References Cited

U.S. PATENT DOCUMENTS 5,736,356   4/1998  Sano et al. .............................. 435/68.1

OTHER PUBLICATIONS

Ramanujam et al., Faseb J. 4(7):A2321, 1990.
Brock et al., Biology of Microorganisms, 4th edition, Prentice–Hall, Inc., Englewood Cliffs, NJ, pp. 725–728, 1984.

*Primary Examiner*—Keith D. Hendricks
*Attorney, Agent, or Firm*—Oblon, Spivak, McClelland, Maier & Neustadt, P.C.

[57] ABSTRACT

A method for processing a protein, a non-proteinaceous amino acid polymer, or a non-proteinaceous amino acid polymer, or a peptide or derivatives thereof having a crosslinked structure, which entails contacting glutamine and lysine residues in a protein, a non-proteinaceous amino acid polymer, a peptide or derivatives thereof with a transglutaminase obtained from *Bacillus subtilus* to form intermolecular or intramolecular, crosslinked $\epsilon(\delta\text{-Glu})\text{-Lys}$ bonds between or in the molecules of the protein, non-proteinaceous amino acid polymer, peptide or derivatives thereof, wherein the transglutaminase has the physicochemical properties described herein.

7 Claims, 9 Drawing Sheets

BACILLUS-DERIVED TRANSGLUTAMINASE

This application is a Division of application Ser. No. 08/596,864, filed on Feb. 9, 1996, now U.S. Pat. No. 5,731,183.

BACKGROUND OF THE INVENTION

1. Field of the Invention

The present invention relates to (1) a transglutaminase (hereinafter referred to as TG) isolated from a Bacilli such as those of *Bacillus subtilis*, (2) a fraction having transglutaminase activity, and (3) a method for producing a protein, a non-proteinaceous amino acid polymer, a peptide or derivatives thereof having a crosslinked structure, by crosslinking the glutamine and lysine residues in the same with the TG or the fraction having TG activity to thereby form intermolecular or intramolecular, crosslinked $\epsilon$-($\gamma$-Glu)-Lys bonds.

The present invention also relates to (4) a DNA coding for a TG derived from a Bacilli such as *Bacillus subtilis*, (5) a vector comprising said DNA coding for said TG, (6) a cell transformed with the vector, and (7) a method for producing a Bacillus-derived transglutaminase by incubating the transformant.

The crosslinked polymers produced using the Bacillus-derived TG of the present invention can be used in foods such as tofu (soybean curd), pudding, yogurt, cheese, ground fish meat, boiled fish paste, sausage and other fish and meat products and also in cosmetics, etc.

2. Discussion of the Background

TG is an enzyme which catalyzes the transacylation of $\gamma$-carboxyamide groups in the glutamine residues in a peptide chain with the either $\epsilon$-amino group in a lysine residue in the peptide chain or water. When a $\epsilon$-amino group is the acyl acceptor, crosslinked $\epsilon$-($\gamma$-Glu)-Lys bonds (hereinafter referred to as "GL bonds") are formed in or between the peptide molecules. Where water is the acyl receptor in the transacylation, the glutamine residue in the peptide chain is subjected to de-amidation by which the glutamine residue is converted into a glutamic acid residue.

It is known that TG exists in many animal tissues. For example, TG existing in the liver of guinea pigs has been studied (see Connellan et al., J. Biol. Chem., Vol. 246, pp. 1093–1098, 1971). Microorganism-derived TGs are less well known, only TG derived from Actinomycetes (ray fungi), *Bacillus subtilis* (see Ramanujam et al., FASEB J. Vol. 4, A2321) and Myxomycetes (slime molds) (see Klein et al., J. Bacteriol., Vol. 174, pp. 2599–2605) have been reported. At present, TG produced by ray fungi has been put to practical and industrial use (see Japanese Patent Publication No. 6-65280, Japanese Patent Laid-Open No. 1-27471).

Unfortunately, TG derived from animals such as guinea pigs is impractical for use in industry because it is difficult to obtain a large amount of such animal-derived TG at low costs. In addition, the animal-derived TG requires calcium ions, thus limiting its use.

Ray fungus-derived TG also has some drawbacks. Since ray fungi grow more slowly than ordinary bacteria, they need a long period of time for incubation, resulting in the increase in the costs in producing TG.

Ramanujam et al. of New Mexico State University have reported the existence of *Bacillus subtilis*-derived TG. The TG as reported by them have the following properties:

1) The pH suitable for it is 9.5 or higher.
2) Since its activity is greatly inhibited by a chelating agent (EGTA), it is considered that the TG has the property of requiring metal ions.
3) It is inhibited by $Ca^{2+}$ of 5 mM or more.
4) It is inhibited by dithiothreitol (DTT).
5) It is produced by both vegetative cells and sporulating cells.

It is considered that TG reported by Ramanujam et al. is limited due to the above-mentioned properties, especially because its operating pH is high and it is influenced by metal ions.

Thus, (1) the animal-derived TG is impractical for industrial use because it requires calcium increasing production costs, (2) the ray fungus-derived TG is impractical for industrial use because the growth of ray fungi is slow increasing production costs, and (3) Ramanujam et al.'s *Bacillus subtilis*-derived TG is impractical for industrial use, since it cannot be used in foods since it is inhibited by 5 mM of $Ca^{2+}$.

SUMMARY OF THE INVENTION

Therefore, the object of the present invention is to isolate a novel TG from a Bacilli that has previously been used in producing foods, such as *Bacillus subtilis*, and to provide a method for producing crosslinked polymers by the use of such TG.

The present inventors have such a TG. The present invention includes a Bacillus-derived TG, and a method for producing crosslinked protein, non-proteinaceous amino acid polymer, peptide or derivatives thereof using the TG, or a fraction comprising the TG. The TG of the present invention has the following physicochemical properties:

a) it is active between about pH 7 and about 9,
b) it is active between about 40° C. and about 65° C.,
c) it is stable at about 60° C. or lower,
d) it is independent of $Ca^{2+}$ and has an activity of 50% or more in the presence of 5 mM of $Ca^{2+}$,
e) it is inhibited by NEM, cystamine and $(NH_4)_2SO_4$,
f) it is not inhibited by EDTA, DTT and 2-ME,
g) it has a molecular weight of (i) from about 18,000 to about 22,000 as measured by gel permeation and (ii) from about 28,000 to about 30,000 as measured by SDS-PAGE, and
h) it catalyzes the transacylation of the $\gamma$-carboxyamide group in glutamine residue(s) in a peptide chain.

The present invention further includes a DNA coding for the above TG, a vector comprising such DNA, a cell transformed with the vector, and a method for producing a Bacillus-derived transglutaminase by incubating the transformant.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
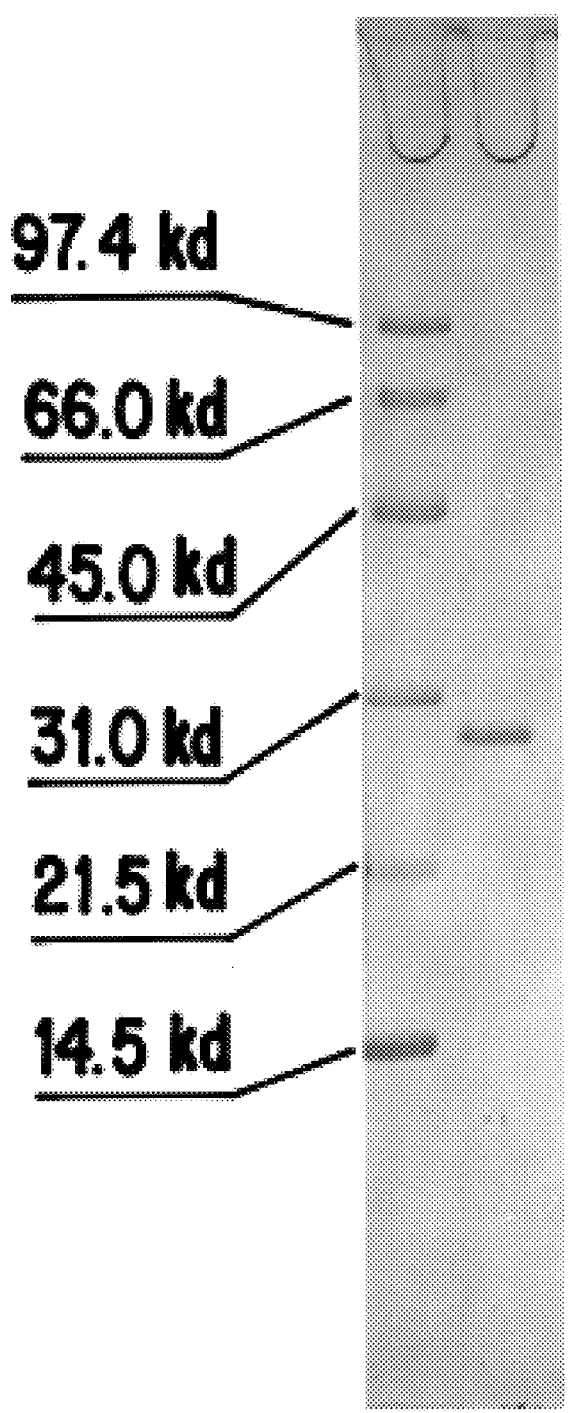
FIG. 1 shows the results of SDS-PAGE of pure TG-1.

Protein, non-proteinaceous amino acid polymer, peptide and derivatives thereof having crosslinked structures can be formed by the action of the TG or the TG activity-having fraction are referred to herein as crosslinked polymers.

The TG of the present invention can be isolated from sporogenic bacteria, such as Bacilli, typically those of *Bacillus subtilis*. Preferably the bacteria are at the sporulation stage. Two preferred strains include *Bacillus subtilis* AJ12866 and *Bacillus subtilis* AJ1307.

*Bacillus subtilis* AJ12866 was deposited on Feb. 2, 1995 in the National Institute of Bioscience and Human-Technology, the Agency of Industrial Science and Technology, the Ministry of International Trade and Industry of Japan (hereinafter referred to as "NIBH") under accession number FERM P-14750. *Bacillus subtilis* AJ12866 was then transferred to the international depository on Dec. 4, 1995, under the provisions of the Budapest Treaty, under international deposit number FERM BP-5325.

*Bacillus subtilis* AJ1307 was deposited on Aug. 22, 1995 in NIBH, under accession number FERM P-15123. *Bacillus subtilis* AJ1307 was then transferred to the international depository on Jan. 18, 1996, under the provisions of the Budapest Treaty, under international deposit number FERM BP-5367.

The TGs of the present invention broadly exist in bacilli having spores. Namely, the TG also exists in *Bacillus licheniformis, Bacillus megaterium, Bacillus stearothermophilus, Bacillus brevis, Bacillus sphaericus, Bacillus polymyxa, Bacillus alcalophilus*, etc.

Bacilli can be incubated using techniques known in the art by liquid cultivation or solid cultivation. In particular, deep aerating and stirring cultivation is industrially advantageous.

Suitable nutrient sources in nutrient media for the bacilli include ordinary carbon sources, nitrogen sources, inorganic salts and other minor nutrients that are generally used in incubation of microorganisms. All nutrient sources known for use with Bacilli can be employed.

During aeration, aerobic conditions are employed. Bacilli can be incubated at any temperature at which they can grow and produce TG. Typically, the incubation temperature is from 10 to 50° C., preferably from 30 to 40° C. Bacilli which are thermophilic bacteria can be incubated at temperatures higher than the above-mentioned range.

The incubation time will vary, depending on the incubation time and other incubation conditions. Preferably, bacilli are incubated for a long period of time such that they produce the largest amount of TG. In general, Bacillus are incubated for from 5 hours to 7 days or so, preferably for from 10 hours to 3 days or so.

The stage at which Bacilli exhibit their TG activity according to the present invention is limited to only the sporulation stage. This is the most significant point in which the TG of the present invention is basically different from the *Bacillus subtilis*-derived TG as reported by the group of the New Mexico State University.

After the incubated cells of Bacilli begin to form spores, their TG activity begins to increase. Then, the TG activity becomes the largest at the sporulation stages IV to VI or so, and thereafter it decreases. TG activity can be slightly detected in the culture but can be detected much more in the grown cells.

The thus-grown cells are disrupted or lysed under low-temperature conditions. The thus-processed cells are centrifuged at 20000×g for 10 minutes. Then, the supernatant fraction and the precipitate fraction are separated from each other, and the TG activity of each fraction is detected. In that manner, it is verified that the precipitate fraction that contains the spores has TG activity. Thus, TG exists on the surfaces of the spores.

To purify the Bacillus-derived TG, the culture comprising the grown cells of Bacilli may be directly processed to obtain a purified TG, but it is advantageous that the sporangia of the grown cells are first disrupted or lysed and then the resulting spores are processed to obtain a purified TG.

By disrupting or lysing the sporangia to be obtained by incubating Bacilli, it is possible to obtain the spores of Bacilli. After the disrupting or lysing treatment, the fraction having TG activity is collected in the insoluble fraction containing the spores. Therefore, it is also possible to concentrate the insoluble fraction to obtain the intended enzyme preparation.

In order to recover the TG activity that has been collected in the insoluble fraction in a soluble fraction (that is, in order to solubilize the TG activity), the following operations are needed.

First, a surfactant such as TRITON X-100 (a polyethylene ether surfactant), alkylglucoside or the like can be added to the insoluble fraction. Second, the spore-containing fraction can be treated with a basic buffer (for example, 20 mM sodium bicarbonate buffer, pH 10). Third, the spore-containing fraction can be suspended in a buffer and heated. In all of the above, the TG activity is recovered in the resulting soluble fraction. For example, by heating the suspension at 10° C. or higher, the TG activity can be recovered in the soluble fraction.

The solubilized TG can be utilized as a gelling agent. By employing any ordinary methods of, for example, gel permeation, ion-exchange chromatography, etc., which can be used for purifying enzyme, the solubilized TG can be further purified. As a result, TG having a higher relative activity can be obtained. The thus-purified TG can be a gelling agent having a higher relative TG activity.

The measurement of the TG activity shall be conducted in the manner mentioned below. $^{14}$C-labeled putrescine and dimethylcasein are used as the substrates, and a sample containing TG is applied to these to make them reacted with each other. The putrescine-bonded dimethylcasein is precipitated with 10% TCA, and the resulting precipitate is adsorbed onto filter paper. Since the radioactivity existing in the filter paper is proportional to the TG activity in the sample, it is possible to quantitatively determine the TG activity in the sample. The radioactivity can be measured with a liquid scintillation counter.

The *Bacillus subtilis* AJ1307-derived TG is hereinafter referred to as TG-1, while the *Bacillus subtilis* AJ12866-derived TG is as TG-2. On the basis of the data of TG-1 and TG-2, the physicochemical properties of TG of the present invention are mentioned below.

Suitable pH Range:

The pH suitable for TG of the present invention falls between about 7 and about 9 or so.

In order to determine the pH range within which the TG is active, various enzymatic reactions with the TG were carried out at 37° C. for 30 minutes.

Suitable Temperature Range:

The temperature range within which the TG is active is between about 40° C. and about 65° C. or so.

In order to determine the temperature range within which the TG is suitably active, various enzymatic reactions with the TG were carried out at pH of 7.5 for 30 minutes.

Temperature Stability:

The TG was stable at about 60° C. or lower.

The TG was subjected to high-temperature treatment at pH of 7.5 for 10 minutes, whereupon the temperature stability of the TG was checked. Even when the TG was subjected to high-temperature treatment at 60° C., it still maintained about 80% of the TG activity.

Influence of Inhibitors:

The Bacillus-derived TG of the present invention is greatly inhibited by NEM (N-ethylmaleimide) and cystamine. In addition, it is also greatly inhibited by $(NH_4)_2SO_4$ (ammonium sulfate).

Influence of DTT and EDTA:

The activity of the Bacillus-derived TG of the present invention increases in the presence of DTT (dithiothreitol). However, the TG activity was not influenced by the presence of EDTA (ethylenediamine-tetraacetic acid).

Influence of $Ca^{2+}$:

The TG of the present invention does not have the property of requiring $Ca^{2+}$ions. Namely, it is a $Ca^{2+}$-independent enzyme. The TG still maintains 50% or more of its activity in the presence of 5 mM of $Ca^{2+}$.

Molecular Weight:

The TG has a molecular weight of (a) from about 18,000 to about 22,000 (as measured by gel permeation) and (b) from about 28,000 to about 30,000 (as measured by SDS-PAGE).

Activity:

The TG catalyzes the transacylation of a substrate, γ-carboxyamide group in the glutamine residue existing in a peptide chain. When the ε-amino group in a lysine residue in the peptide chain is the acyl receptor, intramolecular or intermolecular, crosslinked ε-(γ-Glu)-Lys bonds are formed in or between the peptide molecules. When water is an acyl receptor in the transacylation, the glutamine residue in the peptide chain is subjected to de-amidation by which the glutamine residue is converted into a glutamic acid residue.

As mentioned hereinabove, the properties of TG of the present invention that is derived from *Bacillus subtilis* AJ12866 and *Bacillus subtilis* AJ1307 were obviously different from those of the *Bacillus subtilis*-derived TG as reported by the group of the New Mexico State University.

The TG of the present invention can be used to produce crosslinked polymers. The TG can be used in a variety of forms including (1) a concentrate of the insoluble, spore-containing fraction that is obtained by disrupting or lysing the sporangia of bacilli incubated, (2) a TG activity-having fraction that is obtained by solubilizing the insoluble fraction in various manners, and (3) a purified TG having a high relative activity. Alternatively, any and every other fraction having Bacillus-derived TG activity can be used.

It is also possible to use a Bacillus-derived TG that is obtained by incubating cells transformed with a vector comprising DNA coding for a Bacillus-derived TG. Such a vector can be obtained using methods known in the art such as those mentioned below.

Suitable substrates for the TG or TG-active fraction include one or more of proteins, non-proteinaceous amino acid polymers, peptides and derivatives thereof which contain at least one glutamine residue and at least one lysine residue. The origins and the properties of the proteins are not specifically defined. Suitable proteins include casein, gelatin, and soybean protein. In addition, proteins denatured partly by proteases, etc. can also be employable.

Suitable non-proteinaceous amino acid polymers include amino acid polymers to be produced by chemical synthesis, such as polylysine, etc. The peptides may be those as obtained by chemical synthesis or those as obtained by decomposing natural proteins with acids, alkalis, proteases, etc. Suitable derivatives of such substances include glycoproteins, chemically-modified proteins, etc. Any other protein or fragment thereof can also be used as the substrate for the TG or TG-active fraction, provided that they have lysine and glutamine residues.

The TG or TG-active fraction of the present invention can be added to and reacted with a solution or slurry containing a protein or the like at a substrate concentration of 0.1% or more, whereby a crosslinked polymer product is obtained. The crosslinked polymers to be obtained according to the present invention may be classified into a group of gelled products, a group of highly-viscous products and a group of merely-polymerized products, depending on the degree of crosslinking in them. The present invention encompasses all such crosslinked polymers.

In general, the pH of the reaction solution is from about 4 to about 10, the reaction temperature is from about 5° C. to about 80° C., and the reaction time is from about 10 seconds to about 24 hours. As a result of the reaction, crosslinked polymers (gelled products, highly-viscous products, etc.) are obtained.

Many examples of producing useful proteins such as enzymes, physiologically-active substances, etc. by recombinant DNA technology are known. One advantage of recombinant DNA technology is that it is possible to produce large amounts of useful proteins that exist only slightly in the natural world. To produce the Bacillus-derived TG of the present invention according to such recombinant DNA technology, a DNA coding for the Bacillus-derived TG is needed. The DNA is linked to a vector DNA to construct the intended recombinant DNA.

DNA encoding the Bacillus-derived TG of the present invention can be obtained as mentioned below. First, the amino acid sequence of the purified TG is determined. It is possible to determine the intended amino acid sequence according to the Edman method (see Edman, P., Acta Chem. Scand., 4, 227 (1950)). In addition, it is also possible to determine the amino acid sequence by the use of a sequencer produced by Applied Biosystems Co.

The amino acid sequence of from the N-terminal to the 35th residue of the Bacillus-derived TG of the present invention is shown in the Sequence Listing as SEQ ID NO:1.

On the basis of the thus-clarified amino acid sequence, the base sequence of the DNA that codes for this can be deduced. To deduce the base sequence of the DNA, employed are a universal codon or a codon that is most frequently used in the genes of Bacilli.

On the basis of the thus-deduced base sequence, DNA molecules having from 30 to 50 base pairs or so are synthesized. The method for synthesizing such DNA molecules is described in Tetrahedron Letters, 22, 1859 (1981). The DNA molecules can also be synthesized by the use of a synthesizer produced by Applied Biosystems Co. The DNA molecules can be used as probes, when the whole length DNA that codes for the Bacillus-derived TG is isolated from the Bacillus chromosome gene library. In addition, these can also be used as primers, when the DNA that codes for the Bacillus-derived TG is amplified by PCR. However, since the DNA as amplified by PCR does not include the whole length DNA that codes for the Bacillus-derived TG, the DNA as amplified by PCR is used as the probe and the whole length DNA that codes for the Bacillus-derived TG is isolated from the Bacillus chromosome gene library.

Suitable operations for PCR are described by White et al., in Trends Genet., 5, 185 (1989). The method for preparing the chromosome DNA of bacilli is described in Molecular Biological Methods for Bacillus, John Wiley & Sons, Ltd. (1990), etc. The method for constructing the chromosome gene library of Bacilli, etc., is described in Molecular Biological Methods for Bacillus, John Wiley & Sons, Ltd. (1990), etc. The method of isolating the intended DNA molecule from the gene library by using DNA molecules as probes is described in Molecular Cloning, 2nd Edition, Cold Spring Harbor Press (1989), etc.

To determine the base sequence of the DNA that codes for the Bacillus-derived TG and that has been isolated according to the manner mentioned above, referred to is the method as described in "A Practical Guide to Molecular Cloning", John Wiley & Sons, Inc. (1985). For the base sequencing, also employable is a DNA sequencer produced by Applied Biosystems Co.

One DNA that codes for the Bacillus-derived TG of the invention is shown as SEQ ID NO:2 in the Sequence List. This DNA was isolated from the chromosomal DNA of *Bacillus subtilis* AJ1307. The DNA that codes for the Bacillus-derived TG is not limited to that shown as SEQ ID NO:2 in the Sequence List. The DNA encoding the TG of the present invention can have any base sequence, in accordance with the species and the strain of the Bacillus from which it is derived.

It is possible to artificially mutate the DNA that codes for the TG isolated from the chromosomal DNA of a Bacillus to modify the base sequence of the DNA. One popular method for such artificial mutation is a site-specific mutation method such as that described in Method in Enzymol., 154 (1987). Any artificially-mutated DNAs, if coding for the Bacillus-derived TG, are within the scope of the DNA that codes for the Bacillus-derived TG of the present invention.

Host cells are transformed with the recombinant DNA. The transformant cells that have been transformed to be able to produce the Bacillus-derived TG are incubated in a medium to thereby make the cells produce and accumulate the Bacillus-derived TG in the medium or in the cells, and thereafter the TG is collected.

Cells of *Escherichia coli* AJ13172 that have the recombinant DNA as constructed by linking the DNA coding for the *Bacillus subtilis* AJ1307-derived TG to a vector DNA were deposited with international depository NIBH on Dec. 20, 1995 under the provisions of the Budapest Treaty, under international deposit number of FERM BP-5346.

It is possible to produce a large amount of the Bacillus-derived TG by linking a vector DNA to the DNA that codes for the Bacillus-derived TG to construct a recombinant DNA, then transforming cells with the recombinant DNA to give transformant cells, incubating the transformant cells in a medium to make the cells produce and accumulate the Bacillus-derived TG in the medium and/or in the cells, and collecting the TG.

In many cases where a large amount of protein is desired to be produced by recombinant DNA technology, the protein produced is often intramolecularly associated to give its inclusion body in the transformant that is producing the protein. The advantages of the expression method of producing protein are that the intended protein can be protected from being digested by the protease existing in the cells used and that the intended protein can be easily purified by disrupting the cells followed by centrifuging the resulting cell debris.

The protein inclusion body thus obtained is solubilized with a protein-denaturating agent, then the activity of the thus-solubilized protein is regenerated essentially by removing the denaturating agent, and thereafter the soluble protein is converted into a correctly-folded, physiologically-active protein. There are known many examples relating to the process, and one example is to regenerate the activity of human interleukin-2 (see Japanese Patent Laid-Open No. 61-257931).

To obtain the activated protein from the protein inclusion body, a series of operations for solubilization, regeneration of the activity, etc. is necessary, and such operations are more complicated than those for directly producing the activated protein. However, when a large amount of protein is produced in cells and when the protein thus produced has an influence on the growth of the cells, the protein can be accumulated in the cells in the form of such an inactive protein inclusion body whereby the influence of the protein can be retarded.

As the method for producing a large amount of the intended protein inclusion body, there are known a method of expressing the intended protein by itself under the control of a strong promoter and a method of expressing the intended protein as a fused protein with a different protein that is known to be expressed in large quantities.

In addition, it is also effective to previously insert some restriction protease recognition site into the fused protein at a suitable position, via which the intended protein can be cut out of the fused protein after its expression.

The host cells to be transformed for the production of a large amount of protein by recombinant DNA technology include cells of bacteria, cells of ray fungi, cells of yeasts, mold cells, vegetative cells, animal cells, etc. In general, cells of a colon Bacillus, *Escherichia coli* are preferably employed. This is because there are many prior art techniques for producing a large amount of protein by the use of cells of *Escherichia coli*.

As the promoter for expressing a DNA that codes for the Bacillus-derived TG, usable are promoters which are generally used for making Escherichia coil produce foreign proteins. For example, usable are strong promoters such as T7 promoter, trp promoter, lac promoter, tac promoter, PL promoter, etc.

In order to make the host cells produce the Bacillus-derived TG as a fused protein inclusion body, a gene that codes for another protein, preferably a hydrophilic peptide shall be linked to the upstream or downstream site of the Bacillus-derived TG gene in each host cell to construct a fused protein gene therein. The gene that codes for another protein may be any one that has the ability to increase the amount of the intended fused protein to be accumulated in the host cells and to enhance the solubility of the fused protein after the denaturation and regeneration of the fused protein. As candidates for the gene, for example, mentioned are T7 gene 10, β-galactosidase gene, dehydrofolic acid reductase gene, interferon γ-gene, interleukin-2 gene, prochymosin gene, etc.

When any of these genes is linked to the gene that codes for the Bacillus-derived TG, the codon reading frames for the two genes shall be the same. Either the genes are linked to each other at suitable restriction endonuclease sites or any synthetic DNA having an appropriate sequence is utilized.

In order to increase the amount of the Bacillus-derived TG to be produced by the host cells, it is preferable to link a terminator that has a transcription-terminating sequence to the downstream site of the fused protein gene. The terminator includes, for example, T7 terminator, fd phage terminator, T4 terminator, tetracycline-resistant gene terminator, *E. coil* trpA gene terminator, etc.

As the vector via which the gene that codes for the Bacillus-derived TG or codes for a fused protein composed of the Bacillus-derived TG and another protein is introduced into *Escherichia coli*, preferred is a so-called multicopying vector. The vector includes, for example, pUC plasmids, pBR322 plasmids and their derivatives. In order to favorably conduct the screening of the resulting transformants, it is desirable that the vector contain a marker such as an ampicillin-resistant gene, etc. As such plasmids, various expression vectors having a strong promoter are commercially available (for example, pUC plasmids produced by Takara Shuzo Co., pPROK plasmids produced by Clonetec Co., pKK233-2 produced by Clonetec Co., etc.).

A DNA fragment comprising a promoter, a gene that codes for the Bacillus-derived TG or codes for a fused protein composed of the Bacillus-derived TG and another protein, and a terminator as linked in that order is linked to a vector DNA to construct a recombinant DNA.

Cells of *Escherichia coil* are transformed with the recombinant DNA, and the resulting transformant cells are incubated to make them express and produce the Bacillus-derived TG or the fused protein composed of the Bacillus-derived TG and another protein.

As the hosts to be transformed, any strains which are generally used for expression of foreign genes can be employed. Especially preferred are *Escherichia coli* JM109 (DE3) strain and JM109 strain. The method for transformation and the method for screening the resulting transformants are described in "Molecular Cloning", 2nd Edition, Cold Spring Harbor Press (1989), etc.

Where a fused protein is expressed, it is possible to modify it such that TG can be cut out of the fused protein using a restriction protease which has, as the recognition sequence, a sequence not existing in TG, such as a blood coagulation factor Xa, kallikrein or the like.

As the production media, usable are any ordinary media which are generally used for incubating cells of *Escherichia coli*, such as M9-Casamino medium, LB medium, etc. The incubation conditions and the production-inducing conditions shall be suitably selected in accordance with the vector marker, the promoter, the type of the host cells used, etc.

To recover and collect the Bacillus-derived TG or the fused protein composed of the Bacillus-derived TG and another protein, for example, employable are various methods such as those mentioned below. Where the TG or the fused protein has been solubilized in the incubated cells, the cells are collected and then disrupted or lysed and the thus-obtained, cell debris-containing liquid can be used as a crude enzyme liquid. If desired, the liquid is further subjected to ordinary precipitation, filtration, column chromatography or the like to thereby purify the TG or the fused protein before use.

If desired, a method of purifying the TG or the fused protein by the use of an antibody thereto can also be employed.

Where a protein inclusion body is formed, this is solubilized with a protein-denaturating agent. In this case, the protein inclusion body can be solubilized along with the cells containing it. However, in consideration of the subsequent operations for purification, it is preferable to isolate the inclusion body prior to the solubilization thereof. The isolation of the inclusion body from the cells can be conducted by any known methods. For example, the cells are disrupted and then subjected to centrifugation or the like through which the inclusion body is recovered.

As the protein-denaturating agent with which the protein inclusion body is solubilized, usable are guanidine hydrochloride (for example, at a concentration of 6 M and at a pH of from 5 to 8), urea (for example, at a concentration of 8 M), etc.

The protein-denaturating agent used is removed by dialysis or the like, and the active protein is regenerated. The dialyzing solution to be used for the dialysis may be a tris-HCl buffer, a phosphate buffer or the like. Its concentration may be from 20 mM to 0.5 M and its pH may be from 5 to 8.

It is desirable that the protein concentration during the regeneration step is restricted to be not higher than 500 $\mu$g/ml or so. In order to prevent the thus-regenerated Bacillus-derived TG from being self-crosslinked, it is desirable that the dialysis temperature is not higher than 5° C. To remove the protein-denaturating agent, also employable are a dilution method, an ultrafiltration method, etc., in addition to the above-mentioned dialysis method. Any of these methods are employable to attain the intended regeneration of the activity of the protein.

Where the DNA having the sequence of SEQ ID NO:2 in the Sequence List is used as the DNA that codes for the Bacillus-derived TG, the Bacillus-derived TG having the amino acid sequence shown under the base sequence of SEQ ID NO:2 is obtained. The open reading frame in the DNA ranges from the 118th adenosine residue to the 8692nd cytosine residue.

According to the present invention, it is possible to obtain a novel TG which has heretofore been unknown from microorganisms, bacilli which are usable in the food industry, such as *Bacillus subtilis*, etc.

The novel TG of the present invention is advantageous in that (1) it does not require calcium, being different from any other animal-derived TGs, and therefore its use is not limited and it can be produced at low cost and that (2) the bacilli which produce the TG of the present invention grow faster than ray fungi and therefore the Bacillus-derived TG can be produced at lower costs than the ray fungus-derived TG.

The TG of the present invention is different from the TG as reported by the group of the New Mexico State University, in that (1) the activity of the former is not inhibited by $Ca^{2+}$ of 5 mM or more, (2) the pH range suitable for the former falls from neutral to weak alkaline, (3) the former is not inhibited by DTT, (4) the former is not inhibited by chelating agents such as EGTA, etc., and (5) the former is produced by Bacilli only at the stage of their sporulation.

Since the TG of the present invention can be used for producing crosslinked polymer substances, it can be applied to the industrial production of various foods.

In addition, since the TG of the present invention is derived from bacilli which are practically used in producing foods, its practical value in the food industry is high.

EXAMPLES

Having generally described this invention, a further understanding can be obtained by reference to certain specific examples which are provided herein for purposes of illustration only and are not intended to be limiting unless otherwise specified.

Example 1

Production and purification of TG

Cells of *Bacillus subtilis* AJ1307 were incubated to make them have a sufficient TG activity. Using Schaeffer's medium, the incubation was conducted always at 37° C. by liquid shaking cultivation or liquid aerating and stirring cultivation. The Schaeffer's medium used had a composition comprising 8 g/liter of Bacto-nutrient broth, 1 g/liter of KCl, 0.12 g/liter of $MgSO_4.7H2O$, 1 mM of $CaCl_2$, 10 $\mu$M of $MnCl_2$ and 1 $\mu$M of $FeSO_4$ and had pH of 7.0.

First, cells of AJ1307 strain were incubated in 20 ml of one medium for 24 hours for seed cultivation. 5 ml of the culture comprising the seed cells were again incubated in a series of three batch media of 100 ml each. After the cells reached the latter stage of logarithmic growth phase in each medium, each culture was transferred to 900 ml of another medium. These three batch media were connected in series, where the incubation of the cells was continued. After the cells again reached the latter stage of logarithmic growth phase in each medium, three liters in all of the cultures were transferred to 27 liters of another medium and were further incubated therein while aerating at ¼ vvm and stirring at 350 rpm.

Again, after the cells reached the latter stage of logarithmic growth phase, 30 liters of the culture was transferred to 270 liters of another medium and was further incubated therein while aerating at 1/20 vvm and stirring at 200 rpm. This is the final incubation. After the cells reached the stage of stationary phase, the incubation was further continued for 6 hours. After this, the final incubation was finished. The final culture was rapidly cooled to 20° C. or lower, using cold water. Then, this was centrifuged, using a continuous centrifuger, to collect the cells. The thus-obtained cells were used as the starting material, from which TG was purified in the manner mentioned below.

The TG activity of the enzyme liquids obtained below was determined according to an enzymatic activity measuring method, which is as follows. 50 $\mu$l of a reagent liquid (100 mM Tris-HCl, pH 7.5, 6.3 mg/ml dimethylcasein, 10 nM $_{14}$C-putrescine, 1.2 $\mu$ci) containing 10 $\mu$l of an enzyme liquid to be measured was reacted at 37° C. for 30 minutes, and then 40 $\mu$l of the thus-reacted liquid was adsorbed onto filter paper and fixed thereon with 10% TCA. Next, this was washed three times with a 5% TCA solution, and its radioactivity was counted using a liquid scintillation counter. The thus-counted value was referred to as the TG activity of the enzyme liquid.

1. Washing of cells:

The cells as collected after the incubation were suspended in 50 mM Tris-HCl (pH 7.5) and centrifuged for 30 minutes at 20,000×g to again collect the cells in the precipitated fraction. The operations for such suspension and centrifugation are to wash the cells. Such washing of the cells was repeated for a total of two times.

2. Lysis of cells:

To one part by weight of the thus-washed wet cells, were added 9 parts by weight of Buffer 1 (100 mM Tris-HCl (pH 7.5), 0.5 mg/ml lysozyme, 20 $\mu$g/ml DNase I, 1 mM EDTA, 2 mM phenylmethanesulfonyl fluoride (PMSF)) that had been cooled with ice, and thus the cells were suspended in the buffer. The resulting suspension was stirred on ice for 1 to 3 hours, whereby the cells were lysed.

3. Preparation of spores:

After the lysis, the resulting solution was centrifuged for 30 minutes at 4° C. and at 20,000×g. The TG activity of each of the centrifuged supernatant and the suspension as prepared by suspending the centrifuged precipitate in Buffer 2 (100 mM Tris-HCl (pH 7.5), 1 mM EDTA) was measured. As a result, the TG activity was detected in the precipitate suspension. The precipitate suspension was observed with a microscope, and the result showed that the suspension contained the bacterial spores and the lysed cell debris residue.

The precipitate suspension whose TG activity had been detected was stirred for 30 minutes while cooling with ice. Next, this was again centrifuged for 30 minutes at 20,000×g, and the TG activity of each of the centrifuged supernatant and the suspension as prepared by suspending the centrifuged precipitate in Buffer 2 was measured. As a result, the TG activity was detected in the precipitate suspension.

The operations for such suspension, stirring and centrifugation using Buffer 2 are to wash the spores. Such washing of the spores was repeated for a total of four times. During the operations, the TG activity was always detected in the precipitate fractions. After the spores were thus washed for a total of four times, the last suspension of the precipitate fraction whose TG activity had been detected was observed with a microscope, and the result showed that the suspension contained almost no cell debris residue but contained only the bacterial spores. The microscopic observation further revealed the absence of any germinated spores.

4. Solubilization of TG:

After having been washed, the spores were centrifuged and collected in the precipitate fraction, and these were suspended in Buffer 3 (0.1 M sodium carbonate, 1 mM EDTA, 50 mM dithiothreitol, pH 10.0) that had been previously heated at 37° C. The pH of the resulting suspension was adjusted to 10.0, and then the suspension was stirred for 30 minutes at 37° C. Next, this was centrifuged for 30 minutes at 20,000×g, and the TG activity of each of the centrifuged supernatant and the suspension as prepared by suspending the centrifuged precipitate in Buffer 3 was measured.

As a result, the TG activity was detected in the centrifuged supernatant. The result verifies the solubilization of TG. The TG-containing solution is referred to as a crude TG solution.

5. Precipitation and removal of concomitant Proteins under acidic conditions:

The crude TG solution was filtered through filter paper, and acetic acid was added to the resulting filtrate to thereby make the filtrate have pH of 5.8. Then, the filtrate was stirred at 5° C. for 1 hour. As a result of this operation, a white precipitate was formed, which was considered to be an isoelectric protein precipitate. Next, this was centrifuged at 20,000×g for 30 minutes, whereby the precipitate was separated from the centrifuged supernatant. The precipitate was dissolved in Buffer 3. The TG activity of each of the centrifuged supernatant and the solution of the precipitate was measured. As a result, the TG activity was detected in the centrifuged supernatant.

6. Precipitation of TG with ammonium sulfate:

To the centrifuged supernatant whose TG activity had been detected, was added 1/20 by volume, relative to the supernatant, of 1 M Tris-HCl (pH 7.5). Next, ammonium sulfate was added and dissolved therein at a final concentration of 50% saturation. The pH of the resulting solution was adjusted to 7.5 by adding sodium hydroxide thereto. Next, this was stirred on ice for 2 hours and then centrifuged at 20,000×g for 30 minutes. The thus-centrifuged supernatant was dialyzed against Buffer 4 (25 mM Tris-HCl (pH 7.5), 5 mM sodium azide), while the centrifuged precipitate was dissolved in Buffer 4 and then dialyzed against Buffer 4. Through the dialysis, ammonium sulfate was completely removed, and the TG activity of each of the supernatant fraction and the precipitate fraction was measured. As a result, the TG activity was detected in the fraction of the centrifuged precipitate or, that is, the fraction of the precipitate as formed in the presence of 50%-saturated ammonium sulfate.

7. Hydrophobic chromatography:

The solution whose TG activity had been detected was dialyzed against Buffer 5 (50 mM Tris-HCl, 0.75 M magnesium sulfate, 0.02% (w/v) sodium azide, pH 9.0). The resulting dialysate was centrifuged at 20,000×g for 30 minutes to isolate the supernatant. The thus-obtained supernatant was applied to a hydrophobic chromatography column, PHENYL SEPHAROSE HP (produced by Pharmacia Co.) that had been equilibrated with the buffer. By this operation, the TG was adsorbed onto the gel.

The protein not adsorbed onto the gel (non-adsorbed protein) was washed away, using Buffer 5. Next, the adsorbed protein was eluted, using the buffer containing ethylene glycol as the eluent. In the elution, the magnesium sulfate concentration and the ethylene glycol concentration in the buffer were varied linearly. Namely, the elution was conducted in such a way that the magnesium sulfate concentration in the buffer used was varied linearly from 0.75 M to 0 M while the ethylene glycol concentration therein was varied also linearly from 0% (v/v) to 10% (v/v).

The TG activity of each eluate fraction obtained by the elution was measured with the result that the TG activity was observed in the eluate as eluted at the magnesium sulfate concentration of approximately from 150 to 200 mM and at the ethylene glycol concentration of approximately from 7 to 8% (v/v).

8. Gel permeation:

The fraction having TG activity was concentrated, using an ultrafiltration device (CENTRIPREP, produced by Amicon Co.), and dialyzed against Buffer 6 (25 mM Tris-HCl, 150 mM NaCl, 1% (v/v) ethylene glycol, 0.02% (2/v) sodium azide, pH 8.0). The resulting dialysate was centrifuged at 20,000×g for 10 minutes to collect the resulting supernatant. The thus-obtained supernatant was applied to a gel permeation column, SEPHARACRYL S200HR (produced by Pharmacia Co.) that had been equilibrated with Buffer 6. The TG activity of each fraction as eluted was measured. As a result, the TG activity was detected in the fraction whose molecular weight was estimated to be from about 18,000 to about 22,000 or so.

9. Anion-exchange chromatography:

The TG fraction thus obtained was concentrated through an ultrafiltration membrane and dialyzed against Buffer 7 (25 mM piperazine, 1% (v/v) ethylene glycol, 0.02% sodium azide, pH 10.5). The resulting dialysate was centrifuged at 20,000×g for 10 minutes to collect the supernatant. The thus-obtained supernatant was applied to an anion-exchange chromatography column, MONO-Q (produced by Pharmacia Co.) that had been equilibrated with Buffer 7. By this operation, the TG was adsorbed onto the gel.

The non-adsorbed protein was washed away, using Buffer 7. Next, the adsorbed protein was eluted, using the buffer containing NaCl as the eluent. The elution was conducted in such a way that the NaCl concentration in the buffer used was varied linearly from 0 mM to 500 mM. The TG activity of each eluate fraction obtained by the elution was measured with the result that the TG activity was observed in the eluate as eluted at the NaCl concentration of approximately from 50 mM to 150 mM.

The thus-obtained active fraction was subjected to SDS-PAGE and stained with Coomassie Brilliant Blue. From this, it was confirmed that the TG was purified to show one single band, and it was estimated that the molecular weight of the TG would be from about 28,000 to about 30,000 (see FIG. 1).

The increase in the relative activity of the purified fraction was determined. Concretely, the TG activity of the above-mentioned crude TG solution and that of the purified active fraction were measured. The results showed that the relative TG activity per the unit protein weight of the purified fraction increased to about 600 times of that of the crude solution due to the series of the purification operations. In the method of measuring the activity as employed herein, the relative TG activity of the purified fraction was estimated to be about $2.5 \times 10^4$ dpm/mg/30 min (37° C., pH 7.5).

10. Determination of the amino acid sequence of TG around its N-terminal:

The amino acid sequence around the N-terminal of the TG as purified in the manner mentioned above was determined as follows.

The purified TG fraction of about 10 μg, in terms of the protein therein, was subjected to polyacrylamide gel electrophoresis in the presence of SDS, and the TG in the gel was transcribed onto a membrane filter. From this, the amino acid sequence of the TG starting from its N-terminal was analyzed by the use of a protein sequencer.

Concretely, according to a semi-dry system (see Protein structure Analysis, written by H. Hirano, published by Tokyo Kagaku Dojin) using MILLIBLOT (as produced by Millipore Co.), the intended enzyme was transcribed onto a polyvinylidene fluoride (PVDF) membrane from the gel obtained by the electrophoresis. Next, the N-terminal amino acid sequence of the intended enzyme thus transcribed on the PVDF membrane was sequenced, using a protein sequencer (Model 476 A, produced by ABI Co.).

Thus, the amino acid sequence of the TG comprised of 35 residues from its N-terminal was determined. The amino acid sequence around the N-terminal of the transglutaminase thus sequenced is shown as SEQ ID NO:1 in Sequence List.

Example 2

Determination of pH and temperature ranges suitable for TG:

The pH-dependent variation in the enzymatic activity of the TG was measured according to the method mentioned below, from which the pH range suitable for the TG was determined.

As the buffers for the enzymatic reaction, used were sodium formate buffers (pH: 2.0, 3.0, 3.5, 4.0), sodium acetate buffers (pH: 4.5, 5.0, 5.5, 6.0), Tris-HCl buffers (pH: 7.0, 7.5, 8.0, 8.5, 9.0) and sodium carbonate buffers (pH: 9.0, 9.5, 10.5, 12.0).

To measure the TG activity, the above-mentioned method of using $^{14}$C-labeled putrescine and dimethylcasein as the substrates was employed. Each buffer was added to the reaction system at a concentration of 50 mM. As the enzyme source, used was the previously-prepared pure TG fraction at a concentration of 2 μg/ml. The reaction was conducted at 37° C. for 30 minutes.

The relative values of the enzymatic activity were measured, in accordance with the varying pH values of the individual reaction systems. At pH of 8.2 (when Tris-HCl with pH of 8.5 was used as the buffer), the reaction system showed the highest TG activity, which was referred to as a standard of 100. The results are shown in FIG. 2.

Figure 2:
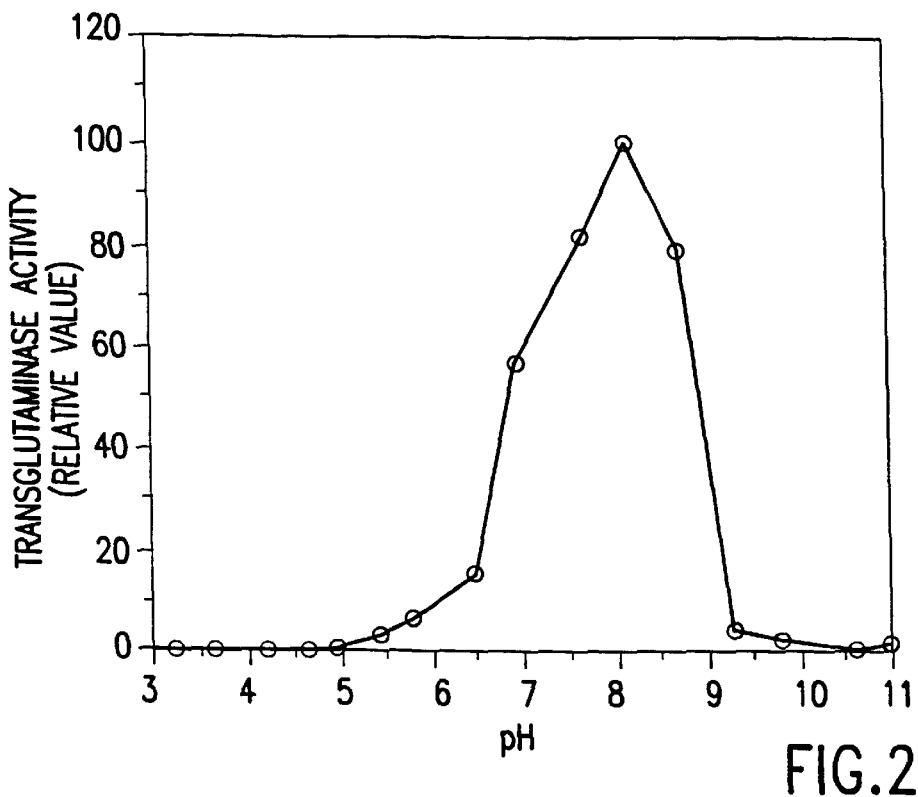
FIG. 2 shows the pH curve relative to the activity of TG-1.

It has been found that the pH range suitable for the TG of the present invention is from about 7 to about 9, strictly from about 7.7 to about 8.8 (see FIG. 2.). On the other hand, the pH range suitable for the *Bacillus subtilis*-derived TG as reported by the group of the New Mexico State University is 9.5 or higher. Therefore, the TG as reported by them is obviously different from the Bacillus-derived TG of the present invention.

The temperature-dependent variation in the enzymatic activity of the TG was measured according to the method mentioned below, from which the temperature range suitable for the TG was determined.

To measure the TG activity, employed was the above-mentioned method of using $^{14}$C-labeled putrescine and dimethylcasein as the substrates. Concretely, the pH of the reaction system was adjusted to 7.5, using 0.1 M Tris-HCl. As the enzyme source, the previously-prepared pure TG fraction was added to the reaction system at a concentration of 2 μg/ml. The reaction system was reacted for 30 minutes in a bath at temperatures varying from 25° C. to 80 C.

Figure 3:
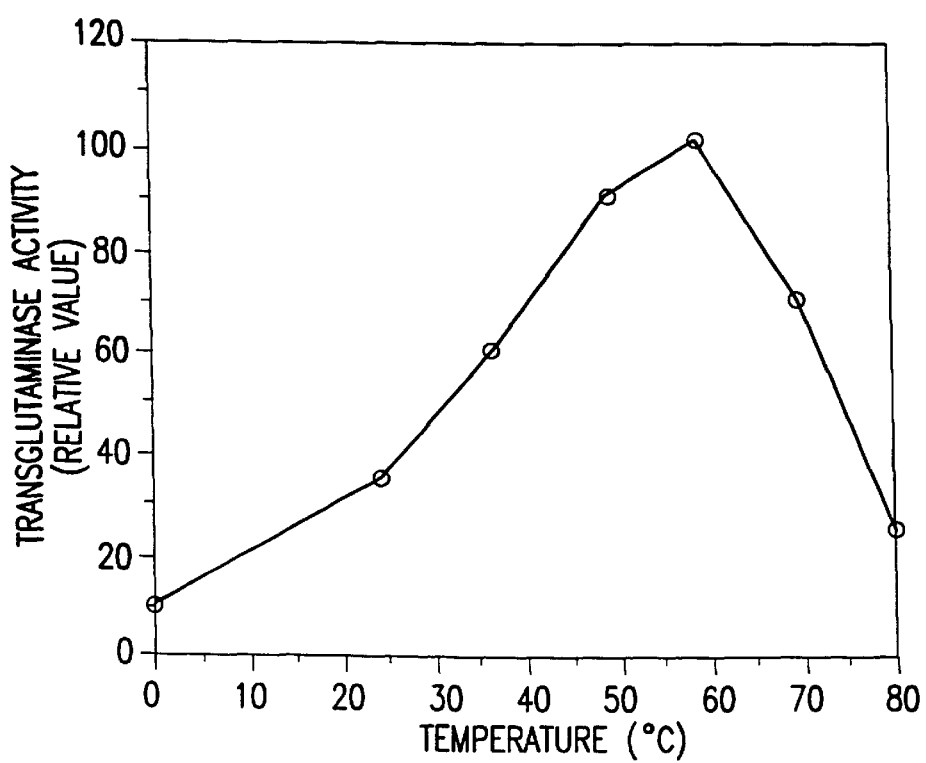
FIG. 3 shows the temperature curve relative to the activity of TG-1.

The relative values of the enzymatic activity were measured in accordance with the varying reaction temperatures. At 60° C., the reaction system showed the highest TG activity, which was referred to as a standard of 100. The results are shown in FIG. 3.

It has been found that the temperature range suitable for the TG of the present invention is from about 40° C. to about 65° C., more strictly from about 50° C. to about 62° C. (see FIG. 3).

Example 3

Determination of temperature stability of TG

The temperature-dependent stability of the TG of the invention was measured according to the method mentioned below.

Figure 4:
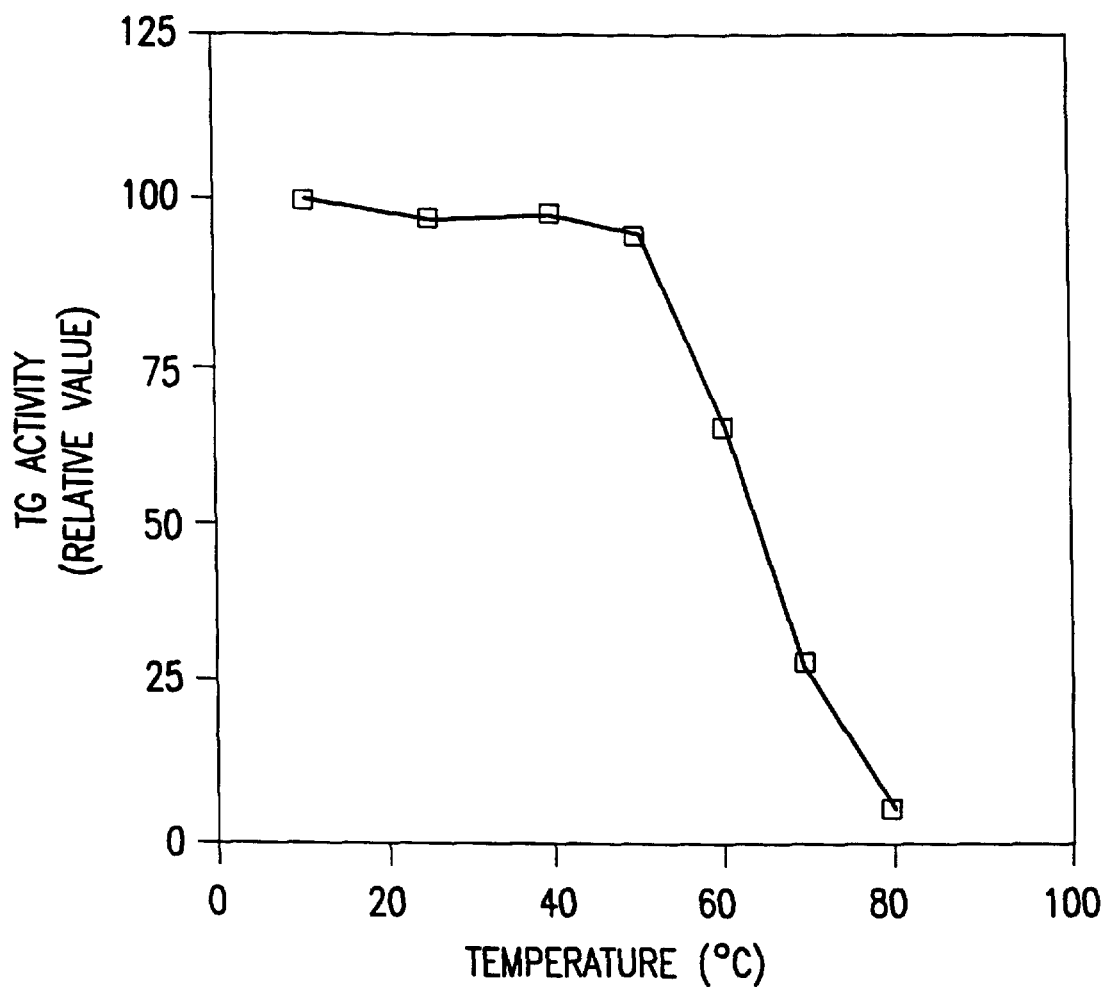
FIG. 4 shows the temperature stability of TG-1.

The previously-prepared pure TG fraction was reacted for 10 minutes in a bath at temperatures varying from 10° C. to 80° C. After this, the TG activity in each system was measured in the same manner as in Example 2. The relative values of the enzymatic activity were measured in accordance with the varying reaction temperatures. The highest TG activity as shown by the reaction system was referred to as a standard of 100. The results are shown in FIG. 4.

It has been found that the TG of the present invention is stable at temperatures not higher than about 60° C. (see FIG. 4).

Example 4

Crosslinking of protein with TG

The protein-crosslinking activity of the TG of the invention was measured according to the method mentioned below.

A reaction system comprising α-casein at a final concentration of 1 mg/ml, 0.1 M Tris-HCl (pH 7.5), 5 mM dithiothreitol and 5 mM sodium azide was prepared.

The α-casein used herein was a commercial product produced by Sigma Co. To this system, added was the previously-prepared pure TG fraction at a final concentration of 440 μg/ml.

The reaction system was reacted for 18 hours in a bath at 37° C. The thus-reacted system was subjected to SDS-PAGE, which gave an additional band at a higher polymer side in addition to the band for the substrate, α-casein. This indicates the cross-linking polymerization of α-casein. The results are shown in FIG. 5.

Figure 5:
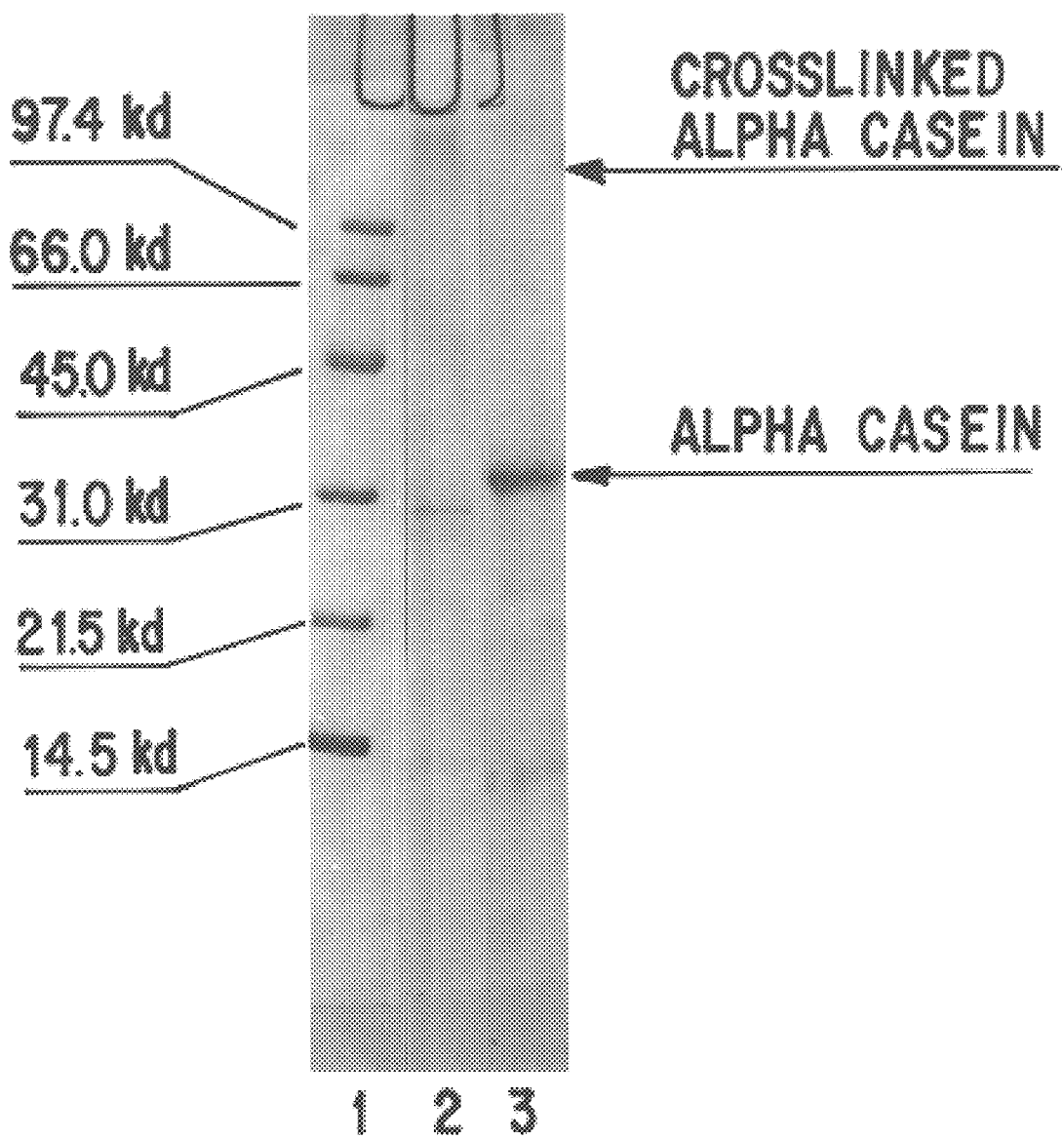
FIG. 5 shows a-casein as crosslinked with TG-1.

These results have verified the protein-crosslinking activity of the TG of the present invention (see FIG. 5).

The same results as above were also obtained when the TG of the present invention was reacted on bovine serum albumin (BSA). That is, the substrate protein BSA was also crosslinked by the TG of the invention.

Example 5

Effects of various reagents on TG activity

Effects, if any, of various reagents on the TG activity were checked. The reagents tested herein were N-ethylmaleimide (NEM), cystamine, phenylmethanesulfonyl fluoride (PMSF), ammonium sulfate, sodium sulfate, EDTA, EGTA, calcium chloride, dithiothreitol (DTT) and 2-mercaptoethanol (2-ME). All were bought from Nacalai Tesque, Inc.

As the enzyme source, the previously-prepared pure TG fraction was used at a concentration of 2 μg/ml. The protein concentration was measured, using a protein assay kit (produced by Bio Rad Co.).

To measure the TG activity, the above-mentioned method of using $^{14}$C-labeled putrescine and dimethylcasein as the substrates (at pH of 7.5 and at 37° C.) was employed. As the enzyme source, the previously-prepared pure TG fraction was used at a concentration of 2 μg/ml. The reaction was conducted at 37° C. for 30 minutes.

The TG activity was measured in the following manner. The above-mentioned pure TG fraction was mixed with each one of the reagents that had been adjusted to have a suitable concentration and then left on ice for 30 minutes. The solution of the enzyme source thus reacted with each reagent was adjusted to have a TG concentration of 2 μg/ml and then reacted with the substrates, whereupon the TG activity still remained in the resulting reaction system was measured (at pH of 7.5 and at 37° C.).

The TG activity of the TG fraction that had not been reacted with any one of the reagents was referred to as 100 (as control), and the TG activity as remained in the reaction system that had been reacted with each reagent was obtained as a relative value to the control. The results are shown in Table 1 below.

| Agent | Concentration | Remaining Activity (relative value) |
|---|---|---|
| — | — | 100 |
| NEM | 1 | 17 |
| cystamine | 2 | 0 |
| PMSF | 5 | 89 |
| (NH$_4$)$_2$SO$_4$ | 10 | 1 |
| Na$_2$SO$_4$ | 10 | 87 |
| EDTA | 10 | 107 |
| EGTA | 10 | 98 |
| CaCl$_2$ | 5 | 65 |
| DTT | 10 | 119 |
| 2-ME | 10 | 111 |

The TG activity of the TG of the present invention was inhibited by NEM, while it was not inhibited by the reducing agents of DTT and 2-ME but was rather enhanced by these to some degree. These results suggest the probability that the cysteine residue will participate in the expression of the TG activity.

The TG of the present invention was not inhibited by DTT, while the *Bacillus subtilis*-derived TG as reported by the group of the New Mexico State University is known to have been inhibited by DTT. That is, the both TGs have obviously different properties.

In addition, the TG of the present invention was not inhibited by sodium sulfate but was inhibited by ammonium sulfate and cystamine. Accordingly, it has been clarified that the TG of the present invention is characterized in that its activity is inhibited in reaction systems containing some amines.

Moreover, the TG of the present invention was not inhibited by the chelating agents of EGTA and EDTA. In view of this property of it, the TG of the present invention is different from the TG as reported by the group of the New Mexico State University. In other words, it can be said that the TG of the present invention does not have the property of requiring metal ions such as $Ca^{2+}$, etc. The reaction systems containing the TG of the present invention, which were used herein for measuring the TG activity, did not contain $Ca^{2+}$, and the TG of the present invention exhibited the TG activity in these $Ca^{2+}$-free reaction systems. From the results, it can be concluded that the TG of the present invention is independent of $Ca^{2+}$.

Furthermore, the TG of the present invention maintained the TG activity of not less than 50% in the presence of Ca2+ of not less than 5 mM. Thus, the TG of the present invention is different from the TG as reported by the group of the New Mexico State University in that the latter is known to have been greatly inhibited by $Ca^{2+}$ of 5 mM or more (see Table 1).

Example 6

TG derived from *Bacillus subtilis* AJ12866 strain was purified, and its properties were determined.

Cells of *Bacillus subtilis* AJ12866 were incubated in a Schaeffer's medium at 37° C. for 16 hours by shaking cultivation. 3 ml of the culture was added to 30 ml of another Schaeffer's medium and further incubated therein at 37° C. for 12 hours. The Schaeffer's media used had a composition comprising 8 g/liter of Bacto-nutrient broth, 1 g/liter of KCl, 0.12 g/liter of $MgSO_4.7H_2O$, 1 mM of $CaCl_2$, 10 μM of $MnCl_2$ and 1 μM of $FeSO_4$ and had pH of 7.0.

The culture was centrifuged at 10,000×g for 20 minutes to separate the precipitate from the supernatant.

The precipitate was ground, using glass beads. The TG activity of each of the culture supernatant, the culture precipitate and the ground precipitate liquid (cell debris liquid) was measured. The method for measuring the enzymatic activity as employed herein was as follows. 50 μl of a reaction system (100 mM Tris-HCl, pH 7.5, 6.3 mg/ml dimethylcasein, 10 nM $^{14}$C-putrescine, 1.2 μCi) containing 10 μl of the enzyme sample to be measured was kept at 37° C. for 30 minutes thereby to make the substrates reacted. After the reaction, 40 μl of the reaction mixture was adsorbed onto filter paper. In the reaction mixture, the putrescine was reacted with the dimethylcasein due to the catalysis of the TG therein. A bonded reaction product of the putrescine and the dimethylcasein was adsorbed on the filter paper. By adding 10% TCA thereto, the bonded reaction product was fixed on the filter paper. Then, the filter paper was washed three times with a 5% TCA solution, and the $^{14}$C radioactivity as fixed to the filter paper was counted with a liquid scintillation counter. The value thus measured corresponds to the relative TG activity of the enzyme sample. The results obtained are shown in Table 2 below.

TABLE 2

| | Relative Activity |
|---|---|
| culture supernatant | 280 |
| culture precipitate | 510 |
| ground precipitate liquid | 10200 |

These results show that the ground precipitate liquid sample which is a fraction containing the bacterial spores has a much higher TG activity than the other samples.

Example 7

Determination of the stage at which the Bacillus-derived TG is induced

Figure 6:
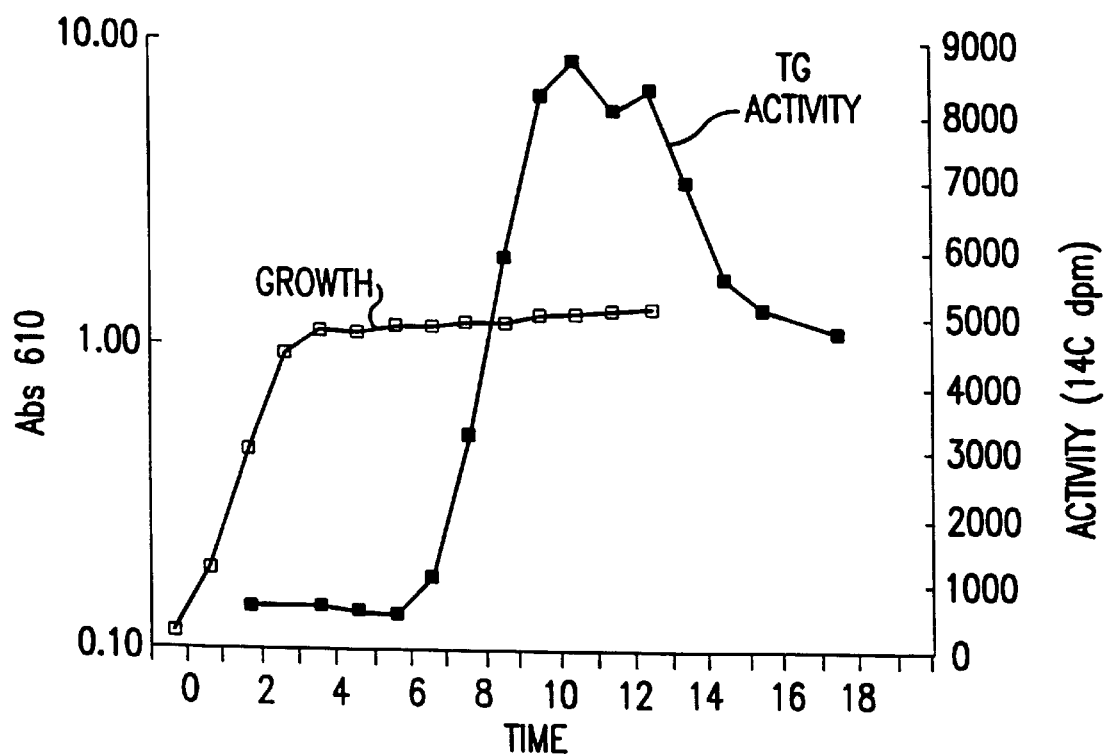
FIG. 6 shows the relationship between the growth of TG-producing cells and the activity of TG-2 produced.

Cells of *Bacillus subtilis* AJ12866 strain were incubated in the same manner as in Example 6, while the TG activity of the cell debris suspension as sampled was measured at given intervals. For the preparation of the cell debris suspension and the measurement of the TG activity, the processes of Example 1 and Example 6 were referred to. The degree of growth of the cells of *Bacillus subtilis* AJ12866 being incubated was represented by the degree of turbidity of the culture. To determine the degree of turbidity of the culture, a ray having a wavelength of 610 nm was applied to the culture and the absorbance of the ray was measured. The results obtained are shown in FIG. 6. As is known from these results, the TG activity of the culture began to increase after the growth of the cells reached the stage of stationary growth and the cells began to form their spores (about 4 hours after the start of the incubation).

Example 8

Purification of Bacillus-derived TG

Using the cells as incubated in the same manner as in Example 7, the following experiments were carried out.

The cells of *Bacillus subtilis* AJ12866 strain were suspended in a reaction system (0.5 mg/ml lysozyme, 20 μg/ml DNase I, 0.1 M Tris-HCl (pH 7.5), 2 mM DTT, 1 mM EDTA, 2 mM PMSF) and reacted on ice for 2 hours whereby the cells were lysed. The resulting reaction mixture was centrifuged at 20,000×g for 20 minutes, and the precipitate fraction thus obtained was suspended in a washing system (0.1 M Tris-HCl (pH 7.5), 1 mM EDTA, 2 mM PMSF). The resulting suspension was centrifuged, and the precipitate was collected. This operation was repeated for a total of two times.

The thus-obtained precipitate fraction was suspended in a buffer (0.1 M sodium carbonate (pH 10), 1 mM EDTA, 2 mM PMSF) and left at 37° C. for 30 minutes. Meanwhile, a part of the substances that had existed in the precipitate fraction were dissolved in the buffer and the TG activity was transferred to the soluble fraction. This was then centrifuged and the resulting supernatant exhibited TG activity. The pH of the supernatant was adjusted to 6.0 by adding acetic acid thereto. This is referred to as a crude enzyme liquid. The crude enzyme liquid was concentrated by ultrafiltration and then dialyzed against a buffer (50 mM Tris-HCl (pH 7.5), 0.1 M NaCl), whereby the buffer was exchanged. The resulting crude enzyme liquid was subjected to gel permeation, and the TG active fraction thus eluted was collected. The enzymatic properties of the fraction were measured.

The results revealed the following facts. For the measurement of the properties, the processes of Examples 1 through 5 were referred to.

Figure 7:
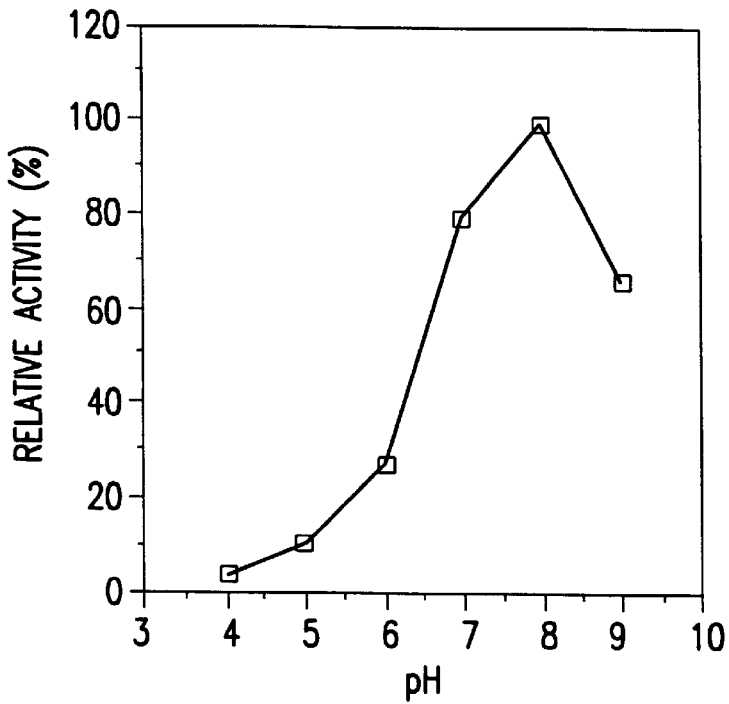
FIG. 7 shows the pH curve relative to the activity of TG-2.
Figure 8:
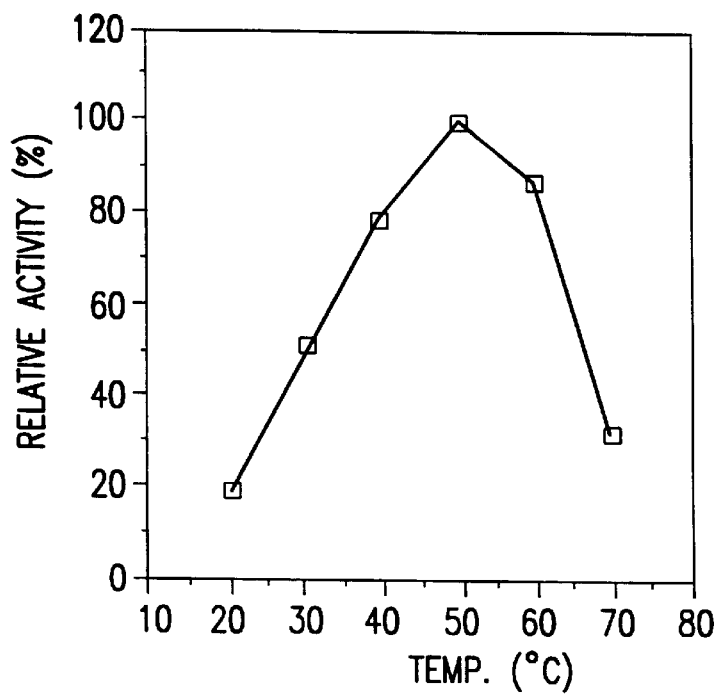
FIG. 8 shows the temperature curve relative to the activity of TG-2.
Figure 9:
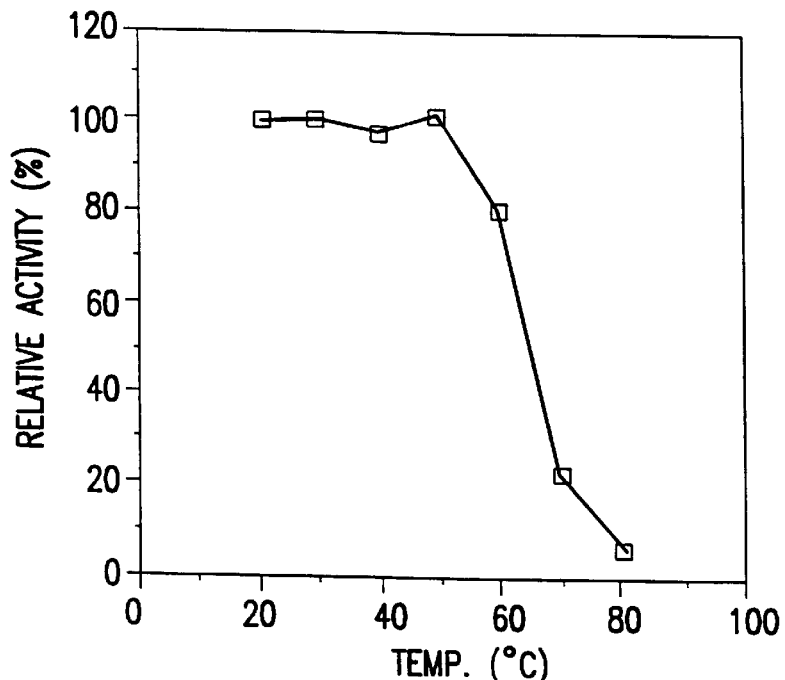
FIG. 9 shows the temperature stability of TG-2.
Figure 10:
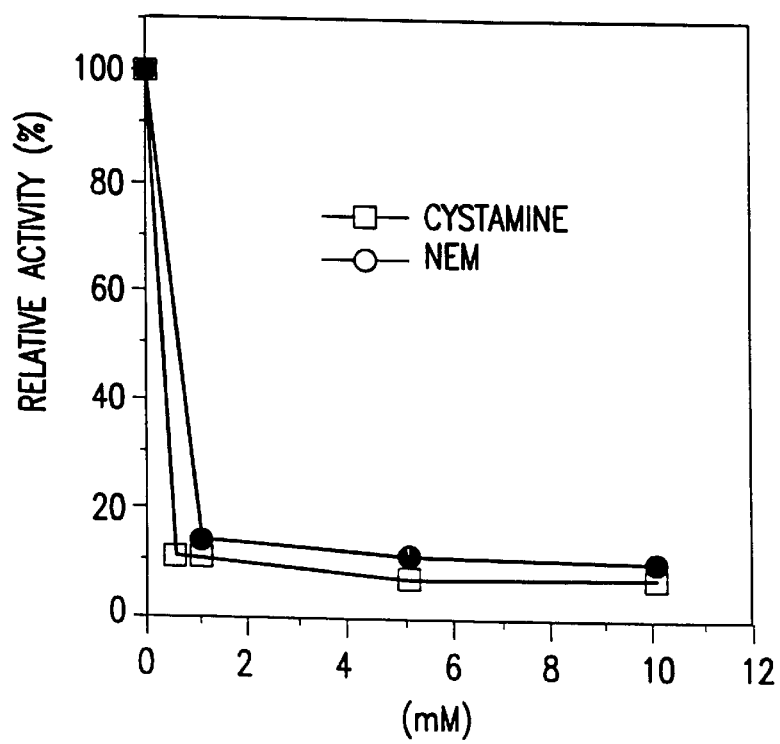
FIG. 10 shows the influence of inhibitors on TG-2.

(1) The pH range suitable for the TG was from about 7 to about 9 (see FIG. 7). (2) The temperature range suitable for the TG was from about 40° C. to about 65° C. (see FIG. 8). (3) Regarding its temperature stability, the TG was stable at about 60° C. or lower (see FIG. 9). (4) The TG was greatly inhibited by cystamine, NEM and $(NH_4)_2SO_4$ (see FIG. 10 and Table 3).

TABLE 3

| Agent | Concentration (mM) | Remaining Activity (Relative value) |
|---|---|---|
| — | — | 100 |
| PMSF | 5 | 95 |
| $(NH_4)_2SO_4$ | 10 | 3 |
| $Na_2SO_4$ | 10 | 85 |
| EGTA | 10 | 94 |
| 2-ME | 10 | 122 |

Figure 11:
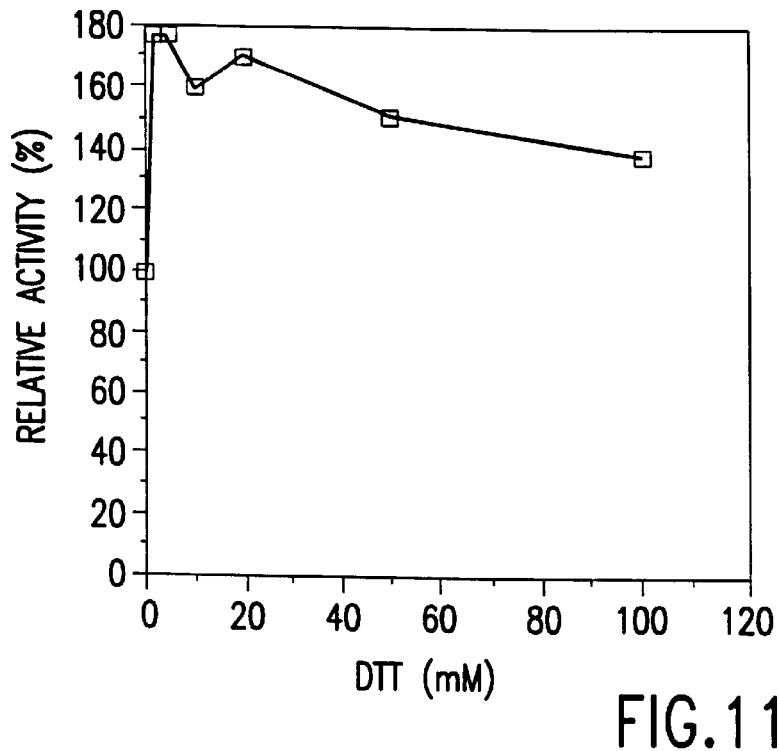
FIG. 11 shows the influence of DTT on TG-2.
Figure 12:
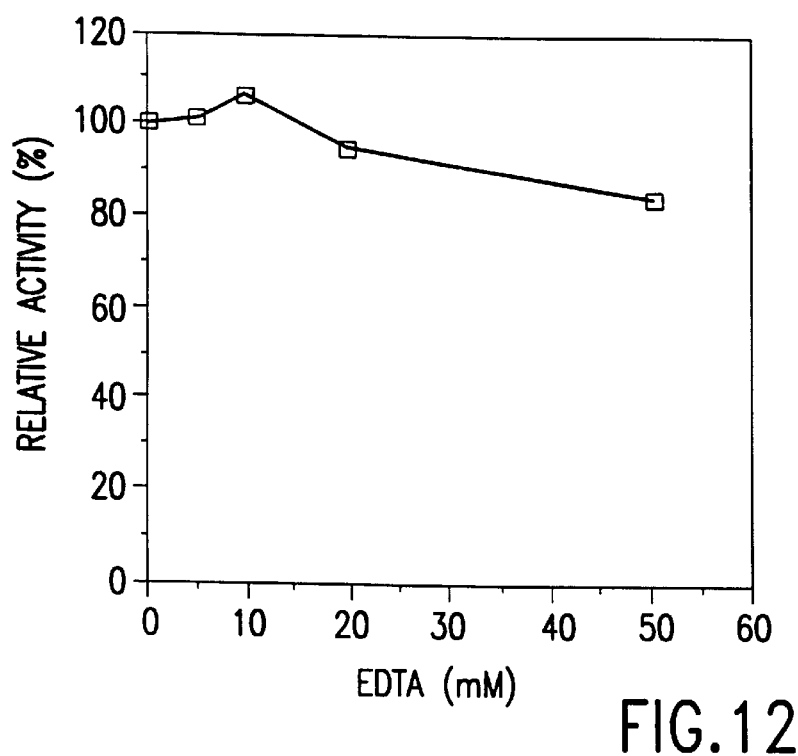
FIG. 12 shows the influence of EDTA on TG-2.
Figure 13:
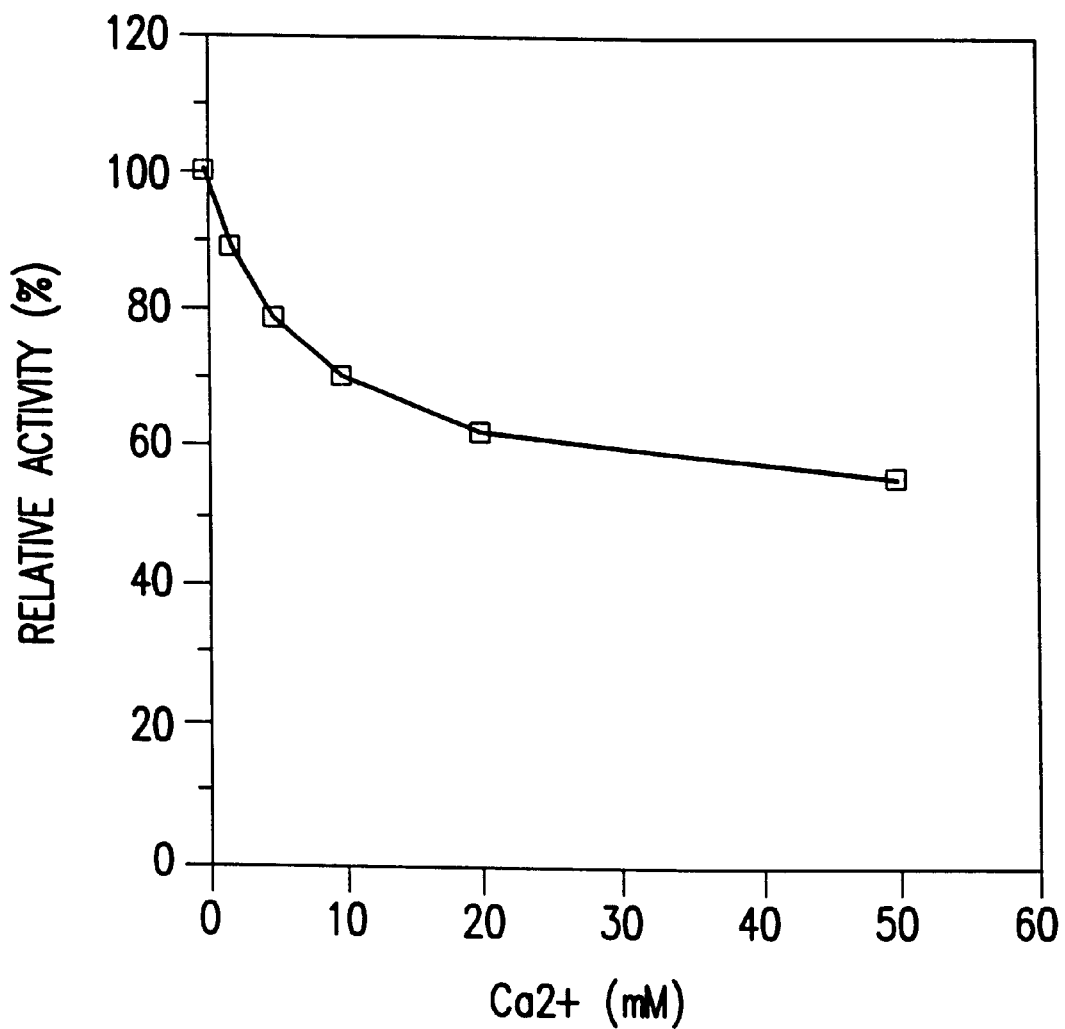
FIG. 13 shows the influence of $Ca^{2+}$ ions on TG-2.

(5) The TG activity was not inhibited by DTT but rather increased by about 1.5 times or more in the presence of 1 mM of DTT (see FIG. 11). (6) EDTA had almost no influence on the TG activity (see FIG. 12). (7) The TG activity was not inhibited by $Ca^{2+}$ of 5 mM or more. The expression of the TG activity does not require the presence of $Ca^{2+}$ ions. In other words, the TG is independent of $Ca^{2+}$ (see FIG. 13). (8) The TG had a molecular weight of (a) from about 18,000 to about 22,000 (as measured by gel permeation) and (b) from about 28,000 to about 30,000 (as measured by SDS-PAGE).

In addition, the amino acid sequence of the TG near its N-terminal or, namely, the amino acid sequence thereof of 35 residues from its N-terminal was determined. The result revealed the high homology of the TG obtained herein to the Bacillus subtilis AJ1307-derived TG obtained previously. Precisely, the amino acid sequences of the two TGs are different from each other only in the 22nd amino acid residue. The AJ1307-derived TG has asparagine residue at the 22nd amino acid residue, while the AJ12866-derived TG has aspartic acid residue at the 22nd amino acid residue.

The results of the above-mentioned experiments show that the TG derived from Bacillus subtilis AJ12866 has the same properties as those of the above-mentioned, Bacillus subtilis AJ1307-derived TG.

Example 9

Gellation of Proteins with TG of the invention

The TG active fraction as obtained after the gel permeation in Example 8 was mixed with a 10% casein solution (25 mM Tris-HCl (pH 7.5), 5 mM DTT) at a ratio of 1:9 and reacted at 37° C. for 24 hours. After the reaction, the solution was gelled.

The pure TG as obtained in Example 1 was added to a 7% gelatin solution at a concentration of 2 units/g-protein and reacted at 35° C. for 2 hours. After the reaction, the gelatin protein solution was gelled.

Example 10

Isolation of Bacillus-derived TG gene (1) Purification of TG and Determination of its N-terminal amino acid sequence:

The partial amino acid sequence of the Bacillus-derived TG as determined in Example 1, which corresponds to SEQ ID NO:1 in the Sequence List, was checked as to whether or not it is homologous to any amino acid sequences of known peptides. However, there was found no homology of the former to any amino acid sequences as registered in Gen-Bank (LASL-GDB), SWISS-PROT and NBRF(PIR).

The amino acid sequence of the TG was back-translated on the basis of the universal codon, from which the base sequence that codes for the amino acid sequence was deduced. Then, the base sequence was checked as to whether or not it is homologous to any base sequences of known nucleic acids. The results revealed the presence of high homology of the former to one base sequence as registered in GenBank (LASL-GDB). The base sequence that was found herein to be homologous to the base sequence of the TG of the invention has an accession number of L29189, and its source is D. W. Hanlon & G. W. Ordal, J. Biol. Chem., Vol. 269, pp. 14038–14046 (1994). This reference naturally discloses the base sequences of genes that code for the transmembrane receptor of Bacillus subtilis, and the base sequence which is disclosed therein and which was now found herein to be homologous to the base sequence of the TG of the invention, is positioned in the upstream flanking region. Concretely, the base sequence of the TG of the invention was found to be homologous to the disclosed base sequence in question of from 1st to 68th base residues. The latter base sequence composed of 68 base pairs is positioned in the 5'-upstream site of the mcpB gene of Bacillus subtilis, and its transcribing direction is opposite to that of the mcpB gene. The functions of the peptide as coded for by the sequence composed of 68 base pairs are not referred to by D. W. Hanlon & G. W. Ordal in J. Biol. Chem. Vol. 269, pp. 14038–14046 (1994).

(2) Collection of cells:

Cells of Bacillus subtilis AJ1307 strain were incubated under the conditions mentioned below. Using Schaeffer's medium, the incubation was conducted always at 37° C. by liquid shaking cultivation. First, cells of AJ1307 strain were incubated in 20 ml of a Schaeffer's medium overnight for seed cultivation. 5 ml of the culture comprising the seed cells was finally incubated in 100 ml of another Schaeffer's medium.

(3) Isolation of chromosome DNA from cells:

After the cells reached the latter stage of logarithmic growth phase under the conditions mentioned above, 100 ml of the culture was centrifuged (at 12,000×g, at 4° C. and for 15 minutes) and the cells were collected. The cells were suspended in 10 ml of 50:20 TE (50 mM Tris-HCl, pH 8.0, 20 mM EDTA), washed and centrifuged to again collect the cells. And, again, the cells were suspended in 10 ml of 50:20 TE. 0.5 ml of a 20 mg/ml lysozyme solution and 1 ml of a 10% SDS solution were added to the resulting suspension, in which the cells were incubated at 55° C. for 20 minutes. After the incubation, a 10:1 TE-saturated phenol of the same volume as that of the suspension was added to the suspension, whereby the suspension was de-proteined. To the thus-separated aqueous layer, 2-propanol of the same volume as that of the layer was added, by which the DNA was precipitated and collected. The thus-obtained DNA precipitate was dissolved in 0.5 ml of 50:20 TE, and then 5 μl of 10 mg/ml RNase and 5 μl of 10 mg/ml Proteinase K were added thereto and reacted at 55° C. for 2 hours. After the reaction, a 10:1 TE-saturated phenol of the same volume as that of the solution was added to the solution, by which the solution was de-proteined. To the thus-separated aqueous layer, added was 24:1 chloroform/isoamyl alcohol of the same volume as that of the layer and stirred, and then the aqueous layer was collected. This operation was repeated for a total of two times. To the final aqueous layer thus obtained, were added a 3 M sodium acetate solution (pH 5.2) at a final concentration of 0.4 M and ethanol of twice the volume of the layer. The DNA as precipitated was collected, washed with 70% ethanol, dried and then dissolved in 1 ml of 10:1 TE.

(4) Preparation of DNA fragment by PCR:

To isolate and amplify the DNA molecule containing the gene that codes for the Bacillus-derived TG, employed was TAKARA LA PCR IN VITRO CLONING KIT (produced by Takara Shuzo Co.). Unless otherwise specifically indicated below, the following experiments were carried out according to the method as instructed in the specification attached to the kit.

5 µg of the chromosome DNA as prepared in the previous process (3) was digested with a restriction enzyme Hind III. Next, the DNA fragment was collected by ethanol precipitation, to which was linked a Hind III cassette. This was again subjected to ethanol precipitation, and the collected DNA was subjected to the first PCR using Primer C1 and Primer S1. The base sequence of Primer C1 used corresponds to SEQ ID NO:4 in Sequence List, and that of Primer S1 to SEQ ID NO:5 in the same. Primer C1 is contained in the TaKaRa LA PCR in vitro Cloning Kit used, of which the base sequence is within the base sequence of the Hind III cassette. The base sequence of Primer S1 is complementary to the region of from the 566th guanosine residue to the 600th adenosine residue in the base sequences of the above-mentioned genes that code for the transmembrane receptor of Bacillus subtilis.

The PCR reaction was conducted for a total of 30 cycles under the conditions mentioned below, using GENEAMP PCR SYSTEM 9600 (produced by Perkin Elmer Co.).
One PCR cycle:
  98° C., 20 seconds
  68° C., 3 minutes Next, the reaction mixture was diluted to 1/100, to which were added Primer C2 and Primer S2 for the 2nd PCR. The conditions for the 2nd PCR were the same as those for the 1st PCR. The base sequence of Primer C2 and that of Primer S2 correspond to SEQ ID NO:6 and SEQ ID NO:7, respectively, in the Sequence List. Primer C2 is contained in the TAKARA LA PCR IN VITRO CLONING KIT used, of which the base sequence is within the base sequence of the Hind III cassette. The base sequence of Primer S2 is complementary to the region of from the 34th thymidine residue to the 68th thymidine residue in the base sequences of the above-mentioned genes that code for the transmembrane receptor of Bacillus subtilis.

After the reaction, 3 µl of the reaction mixture was subjected to 0.8% agarose gel electrophoresis, which verified that a DNA fragment of about 2 kb had been amplified.
(5) Cloning of the PCR-amplified DNA fragment with pUC18:

The PCR-amplified DNA fragment of about 2 kb was cloned by ligating it with pUC18. The cloning was conducted using SURE CLONE LIGATION KIT (produced by Pharmacia Co.). Unless otherwise specifically indicated below, the following experiments were carried out according to the method as instructed in the specification attached to the kit. 400 ng of the thus-amplified DNA fragment of about 2 kb were processed to make the both ends thereof blunt, and then phosphorylated. After the phosphorylation, the DNA fragment was purified and then ligated with PUC18 that had been digested with SmaI. Using the reaction liquid thus containing the ligated DNA fragment, cells of *Escherichia coli* were transformed with the DNA.

From the cells thus transformed, some JMlO9 transformants as intentionally transformed with the pUC18 containing the DNA fragment of about 2 kg were selected by screening. For the screening, referred to was the screening method described in Molecular Cloning, 2nd Edition, Cold Spring Harbor Press (1989).
(6) DNA sequencing of TG gene:

The plasmid which the screened transformants had was prepared in accordance with the method described in Molecular Cloning, 2nd Edition, Cold Spring Harbor Press (1989), from which the base sequence of the amplified DNA fragment of about 2 kb was determined. The sequencing was conducted, using DYE TERMINATOR CYCLE SEQUENCING KIT (produced by ABI Co.) and according to the method as instructed in the specification attached to the kit. The electrophoresis was conducted, using DNA SEQUENCER 373 (produced by ABI Co.).

The sequenced result revealed that the PCR-amplified DNA fragment has a region of from 118th adenosine residue to the 1042nd thymidine residue of the base sequence of SEQ ID NO:2 in the Sequence List. Of the base sequence of SEQ ID NO:2, the region of from 118th adenosine residue to the 852th cytosine residue is the open reading frame. The amino acid sequence of the polypeptide which the ORF codes for can be presumed on the basis of the universal codon. The amino acid sequence in question is shown below along with the base sequence of SEQ ID NO:2.

Of the amino acid sequence, the region of from its N-terminal to the 35th amino acid residue is entirely the same as the amino acid sequence composed of 35 amino acid residues as referred to in the previous process (1). This demonstrates that the PCR-amplified DNA fragment is the intended Bacillus-derived TG gene.

It could be concluded that the difference between the base sequence of SEQ ID NO:2 and that as disclosed by D. W. Hanlon & G. W. Ordal in J. Biol. Chem., Vol. 269, pp. 14038–14046 (1994) would be due to the difference in the strains used between them.

The plasmid having the Bacillus-derived TC gene as inserted thereunto in the direction in which the pUC18-derived lac promoter acts on the gene for transcription is referred to as pBSTG75-11.

Example 11

Cloning of Bacillus-derived TG gene from chromosome DNA library.
(1) Formation of chromosome DNA library:

1 µg of the chromosome DNA as prepared in Example 10 was completely digested with Hind III. The DNA was recovered by ethanol precipitation and then dissolved in 10 µl of 10:1 TE. 5 µl of the resulting solution was mixed with 1 ng of pUC118 (produced by Takara Shuzo Co.) that had been digested with Hind III and then dephosphorylated with BAP, and the DNA was ligated with the pUC118, using DNA LIGATION KIT VER. 2 (produced by Takara Shuzo Co.). 100 µl of competent cells of *Escherichia coli* JM109 strain (produced by Takara Shuzo Co.) were mixed with 3 µl of the thus-ligated reaction mixture, and the cells of *Escherichia coli* JM109 strain were transformed with the DNA. The transformant cells were coated over a suitable solid medium to prepare a chromosome DNA library.
(2) Formation of probe:

As the probe, used was the whole length of the TG gene as obtained in Example 1. Using pBSTG75-11 as the template, this was subjected to PCR with Primer S2 and Primer S3. The PCR was conducted, using TAKARA LA PCR KIT Ver. 2.

100 µl of a reaction system comprising 10 ng of the template, pBSTG75-11, 20 pmol of Primer S2 and 20 pmol of Primer S3 was prepared and reacted. Primer S3 is a 35-mer that is complementary to the region of 35 bases of from 818th base to the 852nd base of the base sequence (SEQ ID NO:2) of the TG gene, and its base sequence corresponds to SEQ ID NO:8 in the Sequence List. The PCR was conducted for a total of 30 cycles under the following conditions.
One PCR cycle:

94° C., 30 seconds
55° C., 30 seconds
72° C., one minute

The DNA fragment thus amplified by the above-mentioned reaction was separated by electrophoresis with 1% agarose gel (SEAPLAQUE GTG, produced by FMC Co.). The intended band was cut out, and the DNA was purified therefrom, using EASY PREP SYSTEM (produced by Pharmacia Co.) and PCR PRODUCTS PREP KIT (produced by Pharmacia Co.). Thus finally, 200 µl of a DNA (4 ng/µl) solution was obtained.

The DNA fragment was labeled with $^{32}$p and used as the probe. Using RANDOM PRIMER DNA LABELING KIT Ver. 2 (produced by Takara Shuzo co.), the probe was labeled with [α-$^{32}$P]dCTP (3000 µCi/mmol) (produced by Amersham Co.), in accordance with the method as instructed in the specification attached to the kit.

(3) Colony hybridization:

One example of colony hybridization is described in Molecular Cloning, 2nd Edition, Cold Spring Harbor Press (1989), which was referred to below.

Colonies of the chromosome DNA library were transferred onto a nylon membrane filter (HYBOND-N, produced by Amersham Co.), which was then alkali-denatured, neutralized and fixed.

The hybridization was conducted, using RAPID-HYB BUFFER (produced by Amersham Co.). Concretely, the filter was dipped in the buffer and subjected to prehybridization at 65° C. for 4 hours. After this, the labeled probe as prepared in the previous process (2) was added to the buffer, in which the hybridization was conducted at 65° C. for 2 hours. Next, the filter was washed with 2×SSC containing 0.1% SDS at room temperature for 20 minutes. Further, this was washed twice with 0.1×SSC containing 0.1% SDS at 65° C. for 15 minutes.

The results of this process verified the production of five colonies that hybridized with the probe.

(4) DNA sequencing of TG gene:

In the same manner as in Example 5, the base sequence of the DNA fragment that had been inserted into pUC118 was determined. The result of this sequencing verified that the DNA has the base sequence of SEQ ID NO:2 in the Sequence List.

Example 12

Expression of Bacillus-derived TG gene in *Escherichia coli*:

(1) Incubation of cells of *Escherichia coli* having recombinant TG gene and expression and induction of the recombinant TG gene in the cells:

The plasmid pBSTG75-11 as obtained in Example 10 has a DNA coding for the Bacillus-derived TG along with a DNA coding for a lacZ protein in such a way that the former DNA has been linked to the downstream site in the latter DNA therein. From its base sequence, it is presumed that the plasmid would be designed to be able to express a fused protein with a peptide having an amino acid sequence of SEQ ID NO:9 in the Sequence List, which is composed of 11 amino acid residues and which has been added to the Bacillus-derived TG before the first methionine residue of the sequence of the TG.

In this experiment, test cells of *Escherichia coli* JM109 transformed with pBSTG75-11 and control cells of *Escherichia coli* JM109 transformed with pUC18 were used. The test cells and the control cells were separately incubated in an LB medium containing 100 mg/ml of ampicillin, at 37° C. by liquid shaking cultivation. Concretely, the cells were implanted in 30 ml of the medium and incubated overnight by shaking cultivation to prepare seed cultures. On the other hand, four flasks each containing 30 ml of a fresh medium were prepared. The seed culture of the test cells of *Escherichia coli* JM109 transformed with pBSTG75-11 was implanted in two flasks at a cell concentration of 5%. The two flasks were referred to as Test Group 1 and Test Group 2. On the other hand, the seed culture of the control cells of *Escherichia coli* JM109 transformed with pUC18 was implanted in the other two flasks at a cell concentration of 5%. The two flasks were referred to as Test Group 3 and Test Group 4. The cells in each group were incubated. After the absorbance at 610 nm became about 0.7, IPTG was added to only Test Group 1 and Test Group 3 at a final concentration of 1 mM. Four hours after this, the incubation of the cells in every group was terminated.

(2) Confirmation of protein induced and expressed:

After the termination of the incubation, the cells in each culture were observed with a microscope. The results showed that only the cells JM109 transformed with pBSTG75-11, to which IPTG had been added, contained a protein inclusion body in themselves.

After the termination of the incubation, 10 ml of each culture was centrifuged (at 12,000×g for 15 minutes) to collect the cells. The cells were suspended in 2 ml of 10 mM Tris-HCl (pH 7.5), washed and again centrifuged to collect the cells. The cells were suspended in 1 ml of the same buffer and disrupted by shaking the resulting suspension along with 0.1 mm zirconia beads for 3 minutes, using MINI-BEAD BEATER (produced by Wakenyaku Co.). The thus-disrupted suspension was subjected to SDS-PAGE and stained with CBB. The results showed that the suspension of Test Group 1 (cells of JM109 transformed with pBSTG75-11 and induced by IPTG) gave a band of from about 29,000 to about 30,000. From the molecular weight thus identified, it was presumed that the cells of Test Group 1 would express the expected fused protein.

(3) Confirmation of TG activity:

The TG activity of the expressed protein was measured. Concretely, 10 µl of the previously-prepared suspension that contained disrupted cells was added to a reaction system containing dimethylcasein and $^{14}$C-labeled putrescine and reacted. After the reaction, the reaction mixture was adsorbed onto filter paper, and the amount of the putrescine as caught by dimethylcasein on the filter paper was measured, using a liquid scintillation counter. The results are shown in Table 4 below.

TABLE 4

| Harboured Plasmid | Induction w/ IPTG | TG activity (dpm) |
|---|---|---|
| pBSTG75-11 Test Group 1 | + | 496 |
| pBSTG75-11 Test Group 2 | − | 0 |
| pUC18 Test Group 3 | + | 0 |
| pUC18 Test Group 3 | − | 0 |

These results verified that the cells JM109 transformed with pBSTG75-11 and induced by IPTG (in Test Group 1) exhibited TG activity.

The *Escherichia coli* KM109 strain transformed with pBSTG75-11 was referred to as *Escherichia coli* AJ13172, which was deposited with the international depository in the Bioengineering Laboratory on Dec. 20, 1995 under the provisions of the Budapest Treaty, under international deposit number FERM BP-5446.

It has now been confirmed that the DNA having the base sequence of SEQ ID NO:2 in the Sequence List codes for an enzyme having TG activity. Namely, it has now been clarified that this DNA has a Bacillus-derived TG gene. In addition, it has also been confirmed that, even when additional DNA that codes for a different peptide is added to this DNA, the resulting combination DNA can express the Bacillus-derived TG gene, and that the fused protein to be expressed by the combination DNA has TG activity.

Moreover, it has been clarified that the fused protein can be intracellularly expressed by the intentionally-transformed cells of Escherichia coli as a protein inclusion body and that the expression of the protein can be controlled by suitable promoters.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method for processing a protein, a non-proteinaceous amino acid polymer, or a peptide or derivatives thereof having a crosslinked structure, which comprises:

contacting glutamine and lysine residues in a protein, a non-proteinaceous amino acid polymer, a peptide or derivatives thereof with a transglutaminase obtained from *Bacillus subtilis* to form intermolecular or intramolecular, crosslinked ε-(γ-Glu)-Lys bonds between or in the molecules of the protein, non-proteinaceous amino acid polymer, peptide or derivatives thereof, wherein said transglutaminase has the following physicochemical properties:

a) it is active between about pH 7 and pH 9,
b) it is active between about 40° C. and about 65° C.,
c) it is stable at about 60° C. or lower,
d) the enzymatic activity of the transglutaminase is not dependent on $Ca^{+2}$ and has an activity of 50% or more in the presence of 5 mM of $Ca^{+2}$,
e) it is inhibited by N-ethylmaleimide, cystamine or ammonium sulfate,
f) it is not inhibited by ethylenediamine-tetraacetic acid, dithiothreitol or 2-mercaptoethanol,
g) it has a molecular weight of (i) from about 18,000 to about 22,000 as measured by gel permeation, and (ii) from about 28,000 to about 30,000 as measured by SDS-PAGE, and
h) it catalyzes the transacylation of the γ-carboxyamide group in glutamine residue(s) in a peptide chain.

2. A method for processing a protein, a non-proteinaceous amino acid polymer, a peptide or derivatives thereof having a crosslinked structure, which comprises:

crosslinking glutamine and lysine residues in a protein, a non-proteinaceous amino acid polymer, a peptide or derivatives thereof with a transglutaminase fraction isolated by fractionating spores obtained by disrupting or lysing sporangia of *Bacillus subtilis*, to thereby form intramolecular or intermolecular, crosslinked ε-(γ-Glu)-Lys bonds between or in the molecules of the protein, non-proteinaceous amino acid polymer, peptide or derivatives thereof.

3. A purified or isolated DNA coding for a transglutaminase obtained from *Bacillus subtilis* having the following physicochemical properties:

a) it is active between pH 7 and about pH 9, b) it is active between about 40° C. and about 65° C., c) it is stable at about 60° C. or lower, d) the enzymatic activity of the transglutaminase is not dependent on $Ca^{+2}$ and has an activity of 50% or more in the presence of 5 mM of $Ca^{+2}$, e) it is inhibited by N-ethylmaleimide, cystamine or ammonium sulfate, f) it is not inhibited by ethylenediamine-tetraacetic acid, dithiothreitol or 2-mercaptoethanol, g) it has a molecular weight of (i) from about 18,000 to about 22,000 as measured by gel permeation, and (ii) from about 28,000 to about 30,000 as measured by SDS-PAGE, and h) it catalyzes the transacylation of the γ-carboxyamide group in glutamine residue(s) in a peptide chain.

4. The DNA of claim 3, which has at least the sequence of from the $118^{th}$ base to the $852^{nd}$ base in the base sequence of SEQ ID NO:2.

5. A vector comprising a DNA coding for a tranglutaminase obtained from *Bacillus subtilis* having the following physicochemical properties:

a) it is active between pH 7 and about pH 9, b) it is active between about 40° C. and about 65° C., c) it is stable at about 60° C. or lower, d) the enzymatic activity of the transglutaminase is not dependent on $Ca^{+2}$ and has an activity of 50% or more in the presence of 5 mM of $Ca^{+2}$, e) it is inhibited by N-ethylmaleimide, cystamine or ammonium sulfate, f) it is not inhibited by ethylenediamine-tetraacetic acid, dithiothreitol or 2-mercaptoethanol, g) it has a molecular weight of (i) from about 18,000 to about 22,000 as measured by gel permeation, and (ii) from about 28,000 to about 30,000 as measured by SDS-PAGE, and h) it catalyzes the transacylation of the γ-carboxyamide group in glutamine residue(s) in a peptide chain.

6. A cell transformed with the vector of claim 5.

7. A method for producing a transglutaminase, which comprises:

a) incubating a cell transformed with a vector comprising a DNA coding for a transglutaminase obtained from *Bacillis subtilis* in a culture medium to thereby produce and accumulate said transglutaminase in the medium or in the cells, and b) collecting the transglutaminase, wherein the transglutaminase has the following physicochemical properties:

a) it is active between pH 7 and about pH 9, b) it is active between about 40° C. and about 65° C., c) it is stable at about 60° C. or lower, d) the enzymatic activity of the transglutaminase is not dependent on $Ca^{+2}$ and has an activity of 50% or more in the presence of 5 mM of $Ca^{+2}$, e) it is inhibited by N-ethylmaleimide, cystamine or ammonium sulfate, f) it is not inhibited by ethylenediamine-tetraacetic acid, dithiothreitol or 2-mercaptoethanol, g) it has a molecular weight of (i) from about 18,000 to about 22,000 as measured by gel permeation, and (ii) from about 28,000 to about 30,000 as measured by SDS-PAGE, and h) it catalyzes the transacylation of the γ-carboxyamide group in glutamine residue(s) in a peptide chain.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Ile Ile Val Ser Gly Gln Leu Leu Arg Pro Gln Asp Ile Glu Asn
1               5                   10                  15

Trp Gln Ile Asp Gln Asn Leu Asn Pro Leu Leu Lys Glu Met Ile Glu
            20                  25                  30

Thr Pro Val
        35
```

(2) INFORMATION FOR SEQ ID NO:2:

(i) SEQUENCE CHARACTERISTICS:
      (A) LENGTH: 1042 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 118..843

(xi) SEQUENCE DESCRIPTION: SEQ ID NO:2:

```
CTGCTTAAAA AGTTTTAAAA TAAAAAATGG AAGAAGTTCT TTTTGGCAGT CTTCTGTCTT        60

TTTAGCTTTC ATTGCCCAAG CTCTTTGCAT ATCTTATATA AACAAGGGGG GCTAAAC          117

ATG ATT ATT GTA TCA GGA CAA TTG CTC CGT CCC CAG GAT ATT GAA AAT         165
Met Ile Ile Val Ser Gly Gln Leu Leu Arg Pro Gln Asp Ile Glu Asn
 1               5                   10                  15

TGG CAG ATT GAT CAA AAT CTG AAT CCG CTG TTA AAA GAG ATG ATT GAG         213
Trp Gln Ile Asp Gln Asn Leu Asn Pro Leu Leu Lys Glu Met Ile Glu
            20                  25                  30

ACG CCT GTT CAG TTT GAT TAT CAT TCA ATT GCT GAA CTG ATG TTT GAG         261
Thr Pro Val Gln Phe Asp Tyr His Ser Ile Ala Glu Leu Met Phe Glu
        35                  40                  45

CTT AAA CTG CGG ATG AAT ATT GTA GCA GCG GCA AAG ACG CTG CAC AAA         309
Leu Lys Leu Arg Met Asn Ile Val Ala Ala Ala Lys Thr Leu His Lys
    50                  55                  60

AGC GGG GCG AAG TTT GCC ACT TTT TTA AAA ACA TAC GGG AAT ACA ACG         357
Ser Gly Ala Lys Phe Ala Thr Phe Leu Lys Thr Tyr Gly Asn Thr Thr
```

| | |
|---|---|
| TAT TGG AGG GTT TCA CCG GAG GGC GCC TTG GAG CTG AAA TAC AGA ATG<br>Tyr Trp Arg Val Ser Pro Glu Gly Ala Leu Glu Leu Lys Tyr Arg Met<br>                85                   90                 95 | 405 |
| CCG CCT TCA AAA GCG ATT CGG GAC ATT GCA GAG AAC GGC CCG TTT TAT<br>Pro Pro Ser Lys Ala Ile Arg Asp Ile Ala Glu Asn Gly Pro Phe Tyr<br>           100                   105                   110 | 453 |
| GCG TTT GAA TGC GCA ACC GCA ATC GTT ATC ATT TAT TAC TTG GCC TTA<br>Ala Phe Glu Cys Ala Thr Ala Ile Val Ile Ile Tyr Tyr Leu Ala Leu<br>           115                   120                   125 | 501 |
| ATC GAT ACA ATC GGT GAA GAT AAA TTC AAT GCC AGC TTT GAC AGA ATT<br>Ile Asp Thr Ile Gly Glu Asp Lys Phe Asn Ala Ser Phe Asp Arg Ile<br>130                   135                   140 | 549 |
| ATT TTA TAT GAC TGG CAT TAT GAG AAA TTG CCG ATC TAT ACG GAA ACA<br>Ile Leu Tyr Asp Trp His Tyr Glu Lys Leu Pro Ile Tyr Thr Glu Thr<br>145                   150                   155                  160 | 597 |
| GGA CAC CAC TTT TTC CTT GGA GAT TGT TTG TAT TTT AAG AAT CCT GAA<br>Gly His His Phe Phe Leu Gly Asp Cys Leu Tyr Phe Lys Asn Pro Glu<br>                 165                   170                   175 | 645 |
| TTT GAT CCG CAA AAG GCG CAA TGG AGA GGC GAA AAT GTG ATT TTA CTG<br>Phe Asp Pro Gln Lys Ala Gln Trp Arg Gly Glu Asn Val Ile Leu Leu<br>           180                   185                   190 | 693 |
| GGG GAA GAT AAA TAT TTT GCC CAT GGT CTT GGA ATC TTA AAC GGA AAG<br>Gly Glu Asp Lys Tyr Phe Ala His Gly Leu Gly Ile Leu Asn Gly Lys<br>           195                   200                   205 | 741 |
| CAA ATT ATA GAT AAG CTG AAT TCT TTT AGG AAA AAA GGA GCC TTA CAG<br>Gln Ile Ile Asp Lys Leu Asn Ser Phe Arg Lys Lys Gly Ala Leu Gln<br>           210                   215                   220 | 789 |
| TCA GCC TAC CTT CTG TCT CAG GCG ACC AGA CTG GAT GTT CCG TCT CTT<br>Ser Ala Tyr Leu Leu Ser Gln Ala Thr Arg Leu Asp Val Pro Ser Leu<br>225                   230                   235                  240 | 837 |
| TTC CGC ATCGTCCGCT AAAAAGCCCC ATCGCCTATT TTCGGGACGA TGGGGTTTCA<br>Phe Arg | 893 |
| AATGCCTTTC GTTTTCGATA GAAGGGGGCT GTGCCGAAAT ATTGGTTCGC AGCCCACTCC | 953 |
| ATTTTTTCAA GGTCATTTCT TGTCACGATT GGATCCTGGC TGCTCCATTT GATAAAGCGG | 1013 |
| ACAAAATAGT AGCCTTTGAT AGGAACCAT | 1042 |

(2) INFORMATION FOR SEQ ID NO:3:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:3:

Met Ile Ile Val Ser Gly Gln Leu Leu Arg Pro Gln Asp Ile Glu Asn
1                5                    10                   15

Trp Gln Ile Asp Gln Asn Leu Asn Pro Leu Leu Lys Glu Met Ile Glu
              20                   25                   30

Thr Pro Val Gln Phe Asp Tyr His Ser Ile Ala Glu Leu Met Phe Glu
              35                   40                   45

Leu Lys Leu Arg Met Asn Ile Val Ala Ala Ala Lys Thr Leu His Lys
    50                   55                   60

Ser Gly Ala Lys Phe Ala Thr Phe Leu Lys Thr Tyr Gly Asn Thr Thr
65                70                   75                   80

Tyr Trp Arg Val Ser Pro Glu Gly Ala Leu Glu Leu Lys Tyr Arg Met
              85                   90                   95

```
Pro Pro Ser Lys Ala Ile Arg Asp Ile Ala Glu Asn Gly Pro Phe Tyr
            100                 105                 110

Ala Phe Glu Cys Ala Thr Ala Ile Val Ile Tyr Tyr Leu Ala Leu
            115                 120                 125

Ile Asp Thr Ile Gly Glu Asp Lys Phe Asn Ala Ser Phe Asp Arg Ile
130                 135                 140

Ile Leu Tyr Asp Trp His Tyr Glu Lys Leu Pro Ile Tyr Thr Glu Thr
145                 150                 155                 160

Gly His His Phe Phe Leu Gly Asp Cys Leu Tyr Phe Lys Asn Pro Glu
                165                 170                 175

Phe Asp Pro Gln Lys Ala Gln Trp Arg Gly Glu Asn Val Ile Leu Leu
            180                 185                 190

Gly Glu Asp Lys Tyr Phe Ala His Gly Leu Gly Ile Leu Asn Gly Lys
            195                 200                 205

Gln Ile Ile Asp Lys Leu Asn Ser Phe Arg Lys Lys Gly Ala Leu Gln
            210                 215                 220

Ser Ala Tyr Leu Leu Ser Gln Ala Thr Arg Leu Asp Val Pro Ser Leu
225                 230                 235                 240

Phe Arg (2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, PRIMER C1
            FOR PCR"

(xi) SEQUENCE DESCRIPTION: SEQ ID NO:4:

GTACATATTG TCGTTAGAAC GCGTAATACG ACTCA                               35

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, PRIMER S1
            FOR PCR"

(xi) SEQUENCE DESCRIPTION: SEQ ID NO:5:

TGGCGCTTGT ACATAAGTGC CGTTATCTGC GCCCC                               35

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, PRIMER S2
            FOR PCR"

(xi) SEQUENCE DESCRIPTION: SEQ ID NO:6:

CGTTAGAACG CGTAATACGA CTCACTATAG GGAGA                               35
```

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, PRIMER S2 FOR PCR"

(xi) SEQUENCE DESCRIPTION: SEQ ID NO:7:

```
ATGATTATTG TATCAGGACA ATTGCTCCGT CCCCA                              35
```

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, PRIMER S3 FOR PCR"

(xi) SEQUENCE DESCRIPTION: SEQ ID NO:8:

```
GCGGACGATG CGGAAAAGAG ACGGAACATC CAGTC                              35
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Met Thr Met Ile Thr Asn Ser Ser Ser Val Pro
1               5                   10
```